US008831313B2

(12) United States Patent
Li et al.

(10) Patent No.: US 8,831,313 B2
(45) Date of Patent: Sep. 9, 2014

(54) METHOD FOR DETECTING MICROORGANISMS, DEVICE FOR DETECTING MICROORGANISMS AND PROGRAM

(75) Inventors: Shenglan Li, Gifu-ken (JP); Takashi Nishida, Gifu-ken (JP); Chizuka Kai, Tokyo (JP); Kunimitsu Toyoshima, Osaka (JP)

(73) Assignees: Kabushiki Kaisha N-Tech, Gifu-Ken (JP); Kabushiki Kaisha Yakult Honsha, Tokyo (JP); Tohoshoji Kabushiki Kaisha, Osaka (JP)

( * ) Notice: Subject to any disclaimer, the term of this patent is extended or adjusted under 35 U.S.C. 154(b) by 118 days.

(21) Appl. No.: 13/805,631

(22) PCT Filed: Jun. 20, 2011

(86) PCT No.: PCT/JP2011/064078
§ 371 (c)(1),
(2), (4) Date: Dec. 19, 2012

(87) PCT Pub. No.: WO2011/162213
PCT Pub. Date: Dec. 29, 2011

(65) Prior Publication Data
US 2013/0109051 A1    May 2, 2013

(30) Foreign Application Priority Data

Jun. 23, 2010    (JP) ................. 2010-143161

(51) Int. Cl.
*G06K 9/00*    (2006.01)
*C12M 1/34*    (2006.01)
*C12Q 1/04*    (2006.01)
*G06T 7/00*    (2006.01)
*C12Q 1/02*    (2006.01)
*G06K 9/62*    (2006.01)

(52) U.S. Cl.
CPC ................. *C12Q 1/04* (2013.01); *C12M 41/46* (2013.01); *G06T 2207/20081* (2013.01); *G06K 9/6269* (2013.01); *G06T 2207/30024* (2013.01); *G06T 7/0012* (2013.01); *G06T 2207/10024* (2013.01); *G06K 9/0014* (2013.01); *C12Q 1/02* (2013.01)
USPC ........................................................ 382/128

(58) Field of Classification Search
None
See application file for complete search history.

(56) References Cited

U.S. PATENT DOCUMENTS

| 6,251,624 | B1 | 6/2001 | Matsumura et al. |
| 7,298,885 | B2 | 11/2007 | Green et al. |
| 7,901,933 | B2 | 3/2011 | Green et al. |
| 2004/0101189 | A1 | 5/2004 | Green et al. |
| 2005/0276456 | A1 | 12/2005 | Yamato et al. |
| 2008/0064089 | A1 | 3/2008 | Green et al. |
| 2009/0315987 | A1 | 12/2009 | Straus |
| 2010/0330610 | A1 | 12/2010 | Green et al. |

FOREIGN PATENT DOCUMENTS

| CN | 1717693 A | 1/2006 |
| JP | 09-187270 A | 7/1997 |
| JP | 11-221070 A | 8/1999 |
| JP | 2000-69994 A | 3/2000 |
| JP | 2001022929 A | 1/2001 |
| JP | 2003-116593 A | 4/2003 |
| JP | 2006-345750 A | 12/2006 |
| WO | 9618167 A1 | 6/1996 |

OTHER PUBLICATIONS

Barbedo, "A Review on Methods for Automatic Counting of Objects in Digital Images," IEEE Latin America Transactions, Sep. 2012, 2112-2124, vol. 10, No. 5.
Bayraktar et al., "Feature extraction from light-scatter patterns of Listeria colonies for identification and classification," Journal of Biomedical Optics, May/Jun. 2006, 034006-1-034006-8, vol. 11, No. 3.
Chen et al., "An automated bacterial colony counting and classification system." Inf Syst Front, 2009, 349-368, vol. 11.
Nabuyuki Otsu, "A Threshold Selection Method from Gray-Level Histograms," IEEE Transactions on Systems, Man, and Cybernetics, Jan. 1979, 62-66, vol. 9, No. 1.

Mukherjee et al., "Bacterial colony counting using distance transform," International Journal of Bio-Medical Computing, 1995, 131-140.

Marotz et al., "Effective object recognition for automated counting of colonies in Petri dishes (automated colony counting)," Computer Methods and Programs in Biomedicine, 2001, 183-198.

Wei Xiong et al., "Cell Clumping Quantification and Automatic Area Classification in Peripheral Blood Smear Images," IEEE, 2009, no page numbers.

Zhang et al., "Application of SVM in the Food Bacteria Image Recognition and Count," International Congress on Image and Signal Processing, 2010, 1819-1823.

The International Preliminary Report on Patentability for corresponding application PCT/JP2011/064078 dated Jan. 8, 2013.

*Primary Examiner* — Stephen R Koziol
*Assistant Examiner* — Amandeep Saini
(74) *Attorney, Agent, or Firm* — Seager, Tufte & Wickhem, LLC

(57) ABSTRACT

A method for detecting microorganisms, which comprises: a training step for forming, by a classifier, feature vectors based on color data on individual points within a subject region of training in a culture medium, mapping the points in the culture medium, that are specified by the feature vectors, on a high-dimensional feature space, and linearly separating a set of the points $\psi$ (x1), that are specified by the high-dimensional feature vectors thus obtained, to thereby color-classify the class (C1) of the culture medium; and a identifying step for forming, by a classifier, feature vectors based on color data on individual inspection points within a region in the culture medium using image data obtained by capturing an image of the culture medium under cultivation, mapping the inspection points (xj), that are specified by the feature vectors, on a high-dimensional feature space, and determining whether or not the mapped points $\psi$ (xj), that are specified by the high-dimensional feature vectors thus obtained, belong to the class (C1) of the culture medium, thereby identifying a colony based on inspection points not belonging to the class (C1) of the culture medium.

14 Claims, 12 Drawing Sheets

DURING IDENTIFICATION (PRODUCTION OF COLONIES)

DISPLAY OF DETECTION RESULT

METHOD FOR DETECTING MICROORGANISMS, DEVICE FOR DETECTING MICROORGANISMS AND PROGRAM

FIELD OF THE INVENTION

The present invention relates to a microorganism detecting method, a microorganism detecting device and a program in which an inspection subject such as foods is inspected by detecting microorganisms such as eukaryotes and bacteria such as *Escherichia coli*.

BACKGROUND OF THE INVENTION

Patent Document 1 discloses a method for detecting microorganisms contained in foods and the like. According to the detection method disclosed in this document, images of a plate for microbial detection are captured by a CCD line sensor before and after cultivation. The obtained image data are compared to count microbial colonies. Patent Document 2 discloses a method for detecting microorganisms by using color data specified in advance.

In the detection method of Patent Document 1, colonies are counted by simply comparing image data. Therefore, when relative positions between a camera and a medium are changed before and after cultivation or when the color of the medium and the color of microorganisms are similar, detection accuracy of microorganisms may not be sufficiently ensured. In the detection method of Patent Document 2, microorganisms are detected by using color data specified in advance. Therefore, when the color of microorganisms is changed or when the color of a medium and the color of microorganisms are similar, detection accuracy of microorganisms may not be sufficiently ensured.

PRIOR ART DOCUMENT

Patent Document

Patent Document 1: Japanese Laid-Open Patent Publication No. 2000-69994
Patent Document 2: Japanese Laid-Open Patent Publication No. 11-221070

SUMMARY OF THE INVENTION

Accordingly, it is an objective of the present invention to provide a microorganism detecting method, a microorganism detecting device and a program that allow accurate detection of microbial colonies produced in an inspection subject medium.

To achieve the foregoing objective and in accordance with a first aspect of the present invention, a microorganism detecting method for detecting a microbial colony cultivated in a medium is provided. The method includes a training step and an identifying step. The training step includes: capturing a color image of a learning subject with or without a microbial colony within a medium region, setting at least a part of the medium region as a training subject region within the captured color image; obtaining, as learning data, color data of either or both of medium points and microorganism points within the training subject region; supplying the learning data to a classifier to obtain feature vectors of the color data; and separating, by the classifier, a set of points specified by the feature vectors to classify at least one of a class of medium and a class of microorganisms. The identifying step includes: supplying, to the trained classifier, color data of each inspection point within an inspection subject region corresponding to at least a part of the medium region in a color image of an inspection subject captured in order to inspect the presence or absence of a microbial colony in the medium region, thereby obtaining a feature vector of the color data; determining, by the classifier, to which class a point specified by the feature vector belongs among the classes classified in the training step; and identifying a colony based on the result of the determination.

According to this configuration, in the training step, color data of either or both of the medium points and the microorganism points is supplied to the classifier as learning data, thereby obtaining feature vectors of color data. The classifier separates a set of points specified by the feature vectors and at least one of the class of medium and the class of microorganisms is classified by color. In the identifying step, color data of each inspection point within the inspection subject region in the color image of the inspection subject is supplied to the trained classifier, thereby obtaining a feature vector of the color data. The classifier determines to which class a point specified by the feature vector belongs and identifies a colony based on the result of the determination. Accordingly, it can be determined whether it is a medium or microorganisms in the feature space in which at least one of the medium and microorganisms can be classified by color (separated). Accordingly, even when the color of a colony changes or is similar to the color of a medium, the colony can be accurately identified. Even when the relative positions of image capturing means and an inspection subject shift more or less between training and identification, the colony can be accurately detected. Accordingly, microbial colonies produced in an inspection subject can be accurately detected.

In the training step of the above described microorganism detecting method, the color data of the medium points within the training subject region in the captured color image of the learning subject without a microbial colony in the medium region is preferably supplied to the classifier as the learning data to obtain feature vectors of the color data, the class of medium is preferably classified by the classifier, by setting a threshold at a position distant outward by a predetermined distance from a set of points specified by the feature vectors. In the identifying step, color data of each inspection point within the inspection subject region in the captured color image of the inspection subject is preferably supplied to the trained classifier to obtain a feature vector of the color data, it is preferably determined, by the classifier, whether or not the inspection point specified by the feature vector belongs to the class of medium, and a colony is preferably identified based on the inspection point that has been determined to not belong to the class of medium.

According to this configuration, the classifier is trained for color data of the medium, and in the identifying step, a colony is identified based on inspection points that have been determined to not belong to the class of medium. In this case, it is sufficient that a simple training on the medium be carried out. Thus, the detection process is relatively simple.

In the training step of the above described microorganism detecting method, the color data of the medium points and the color data of the microorganism points within the training subject region in the captured color image of the learning subject are preferably supplied to the classifier as the learning data to obtain feature vectors of the color data, and a set of medium points and a set of microorganism points specified by the feature vectors are preferably separated by the classifier to classify the class of the medium and the class of microorganisms. In the identifying step, color data of each inspection point within the inspection subject region in the captured color image of the inspection subject is preferably supplied to the trained classifier to obtain a feature vector of the color data, it is preferably determined, by the classifier, to which of the class of medium and the class of microorganisms the inspection point specified by the feature vector belongs, and a colony is preferably identified based on the inspection point that has been determined to belong to the class of microorganisms.

According to this configuration, the classifier is trained on color data of the medium and the microorganism points, and classifies the class of medium and the class of microorganisms. In the identifying step, the trained classifier determines to which class the inspection point belongs among the class of medium and the class of microorganisms, thereby identifying a colony. Thus colony detection accuracy is further increased.

In the training step and the identifying step of the above described microorganism detecting method, the data supplied to the classifier preferably includes, in addition to the color data, at least one of shape data and area data.

According to this configuration, at least one of shape data and area data other than color data is supplied to the classifier during training. Thus colony detection accuracy is further increased.

In the training step of the above described microorganism detecting method, separately from the classification of the classes, noise data on noise points within the medium region are preferably collected. In the identifying step, it is preferably discriminated whether or not the inspection point belonging to the class of microorganisms is the noise point based on the noise data. A colony is preferably identified based on the inspection point that has been discriminated not to be the noise point.

According to this configuration, noise data are collected in the training step. In the identifying step, it is discriminated whether or not the inspection points belonging to the class of microorganisms are noise points based on the noise data. A colony is identified based on the inspection points that have been discriminated not to be the noise points. Thus it can be prevented that noise points within the medium region are detected as microorganism points.

In the identifying step of the above described microorganism detecting method, the medium region is preferably divided into a peripheral region and a central region, the identification is preferably carried out using the central region of the medium as the inspection subject region, and the colony is preferably detected for the peripheral region based on a color edge detected by color edge detection.

According to this configuration, within the central region in the medium, a colony is detected based on the result of determination as to whether or not the inspection point specified by the feature vector belongs to the class. On the other hand, within the peripheral region in the medium, a colony is detected based on a color edge detected by color edge detection. Thus colonies can be accurately detected through overall region in the medium region.

In the training step of the above described microorganism detecting method, the inspection subject during a predetermined period from the start of cultivation until before production of a colony is preferably used as the learning subject in order to train the classifier for learning the medium points, thereby classifying the class of medium. In the identifying step, a color image of the inspection subject after the predetermined period is preferably used.

According to this configuration, the inspection subject during a predetermined period from the start of cultivation until before production of a colony is used as the learning subject during training. At identification, a color image of the inspection subject after the predetermined period is used. By using the inspection subject for training, detection accuracy can be increased and training and identification can be carried out in a relatively effective manner.

To achieve the foregoing objective and in accordance with a second aspect of the present invention, a microorganism detecting device for inspecting presence or absence of a microbial colony cultivated in a medium is provided. The device includes training means and identifying means. Training means captures a color image of a learning subject with or without a microbial colony within a medium region, setting at least a part of the medium region as a training subject region within the captured color image, obtains, as learning data, color data of either or both of medium points and microorganism points within the training subject region, has a classifier, and supplies the learning data to the classifier to obtain feature vectors of the color data. The classifier separates a set of points specified by the feature vectors to classify at least one of a class of medium and a class of microorganisms. The identifying means supplies, to the trained classifier, color data of each inspection point within an inspection subject region corresponding to at least a part of the medium region in a color image of an inspection subject captured in order to inspect the presence or absence of a microbial colony in the medium region, thereby obtaining a feature vector of the color data, determines, by the classifier, to which class a point specified by the feature vector belongs among the classes classified by the training means, and identifies a colony based on the result of the determination.

According to this configuration, the same effects as the above microorganism detecting method can be obtained.

To achieve the foregoing objective and in accordance with a third aspect of the present invention, a program configured to cause a computer to execute a microorganism detection process for detecting a microbial colony cultivated in a medium is provided. The program causes the computer to execute a training step and an identifying step. The training step includes capturing a color image of a learning subject with or without a microbial colony within a medium region, setting at least a part of the medium region as a training subject region within the captured color image; obtaining, as learning data, color data of either or both of medium points and microorganism points within the training subject region; supplying the learning data to a classifier to obtain feature vectors of the color data; and separating, by the classifier, a set of points specified by the feature vectors to classify at least one of a class of medium and a class of microorganisms. The identifying step includes: supplying, to the trained classifier, color data of each inspection point within an inspection subject region corresponding to at least a part of the medium region in a color image of an inspection subject captured in order to inspect the presence or absence of a microbial colony in the medium region, thereby obtaining a feature vector of the color data; determining, by the classifier, to which class a point specified by the feature vector belongs among the classes classified in the training step; and identifying a colony based on the result of the determination.

According to this configuration, a computer executes the training step and the identifying step. Accordingly, the same effects as the above microorganism detecting method can be obtained.

In the identifying step of the above described microorganism detecting method, the area of a colony candidate corresponding to a closed region containing a series of inspection points determined to belong to the class of microorganisms is preferably determined. When the area fulfills area conditions defined according to the species of microorganisms, the colony candidate is preferably identified as a colony.

In the training step and the identifying step of the above described microorganism detecting method, at least the color data and the shape data are preferably supplied to the classifier. In the training step, color data and shape data of the colony are preferably supplied to the classifier as learning data to obtain feature vectors of the color data and the shape data, and the class of colonies is preferably classified by the classifier by separating a set of points specified by the feature vectors. In the identifying step, the inspection point is preferably a colony candidate point represented by a region distinguished by color within the inspection subject region, color data and shape data of the colony candidate point are preferably supplied to the trained classifier to obtain feature vectors of the color data and the shape data, it is preferably determined by the classifier whether or not a point specified by the feature vectors belongs to the class of colonies, and a colony is preferably identified based on the result of the determination.

In the above described microorganism detecting method, the classifier preferably includes at least one of a support vector machine based on Kernel method, a neural network, and a Gaussian mixture model.

In the above described microorganism detecting method, the classifier is preferably a support vector machine based on Kernel method. In the training step, high-dimensional feature vectors are preferably obtained by mapping feature vectors of color data of either or both of the medium points and the microorganism points on a high-dimensional feature space according to Kernel method by using a mapping section of the classifier, and a set of points specified by the high-dimensional feature vectors is preferably linearly separated by the classifier to classify at least one of the class of medium and the class of microorganisms. In the identifying step, a high-dimensional feature vector is preferably obtained by mapping the feature vector of the color data of the inspection point on a high-dimensional feature space according to Kernel method by using the mapping section of the classifier, it is preferably determined by the classifier to which class a point specified by the high-dimensional feature vector belongs among the classes classified in the training step, and a colony is preferably identified based on the result of the determination.

According to this method, sets of points specified by high-dimensional feature vectors obtained by mapping the point on a high-dimensional space by Kernel method are linearly separable. Thus classification of classes can be appropriately carried out and microorganisms can be accurately detected.

The above described microorganism detecting device preferably includes image capturing means for obtaining the color image and notification means, which issues a notification that a colony has been detected when the identification means identifies a colony.

DETAILED DESCRIPTION OF THE PREFERRED EMBODIMENTS

First Embodiment

One embodiment according to the present invention will be described hereinbelow by referring to FIGS. 1 to 11.

Figure 1:
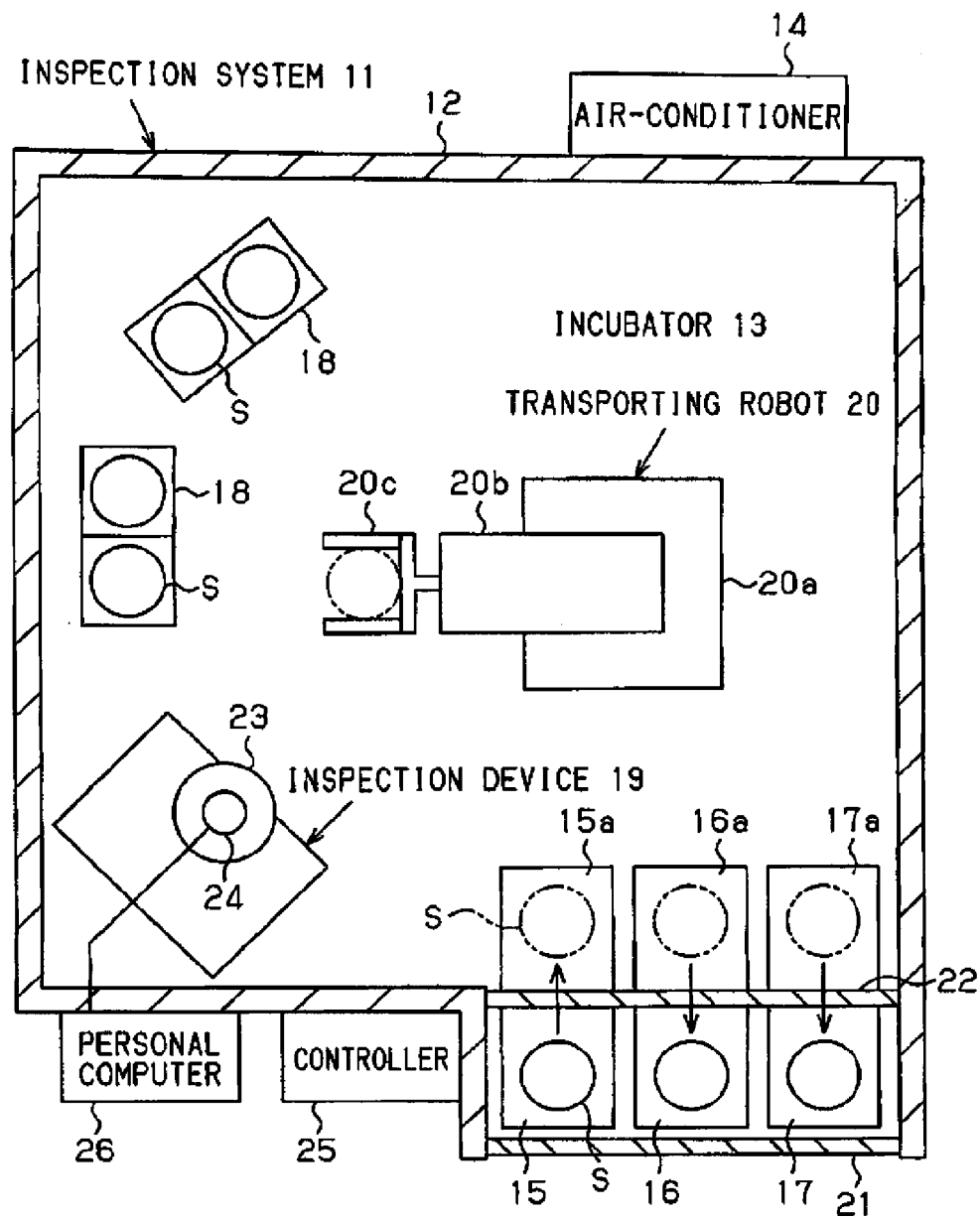
FIG. 1 is a schematic plan view showing an inspection system according to a first embodiment of the present invention.

As shown in FIG. 1, a microorganism inspection system (hereinafter simply referred to as "inspection system 11") includes a constant temperature room 13 enclosed with a wall 12. The temperature in the constant temperature room 13 is maintained at a predetermined temperature by an air-conditioner 14. The inspection system 11 includes, in the constant temperature room 13 at the right lower part in FIG. 1, a feeding shelf 15, a discharge shelf 16 and a discharge shelf 17. From the feeding shelf 15, a sample S (e.g., a petri dish containing a medium), which is an example of the inspection subject, is fed into the constant temperature room 13. From the constant temperature room 13, a sample S having a fair inspection result is discharged through the discharge shelf 16 and a sample S having an inferior inspection result is discharged through the discharge shelf 17. The constant temperature room 13 includes a plurality of storage shelves 18, a microorganism inspection device (hereinafter simply referred to as "inspection device 19") for inspecting a sample S and a transporting robot 20. Samples S fed into the constant temperature room 13 are stored in each of the storage shelves 18 for cultivation. The transporting robot 20 transports samples S between the shelves 15 to 18 and the inspection device 19. The shelves 15 to 17 respectively include conveyors 15a to 17a, which connect inside and outside of the constant temperature room 13. When a sample S is fed and discharged, dual shutters 21 and 22 respectively provided at the outside edge and in the middle of the conveyors 15a to 17a are sequentially opened one by one, thereby preventing entering of microorganisms or the like from the outside into the constant temperature room 13.

The transporting robot 20 includes a rotating main body 20a arranged on the floor of the constant temperature room 13 and an arm 20b having a plurality of joints, which is extended from the main body 20a. A sample S is grasped firmly by a chuck member 20c at the tip of the arm 20b and transported between each of the shelves 15 to 18 and the inspection device 19.

The inspection device 19 includes an inspection bench 23 (inspection stage) for placing a sample S thereon and a camera 24 for capturing an image of a sample S on the inspection bench 23. A sample S stored in the storage shelf 18 is regularly inspected by the inspection device 19 during a cultivation period. The inspection device 19 detects, based on a color image of a sample S captured by the camera 24, a microbial colony in a medium of the sample S. A sample S that has completed a predetermined cultivation period without detectable colonies is discharged through the discharge shelf 16 for fair samples. On the other hand, a sample S having a detectable colony is discharged through the discharge shelf 17 for inferior samples.

The inspection system 11 includes, outside of the constant temperature room 13, a controller 25 and a personal computer 26. The controller 25 controls the air-conditioner 14, the transporting robot 20, the conveyors 15*a* to 17*a*, the shutters 21 and 22 and the like. The personal computer 26, which is part of the inspection device 19, receives color image data of a sample S captured by the camera 24. The personal computer 26 performs a microorganism detection process, in which a colony is detected by discriminating between a medium and microorganisms in a sample S using color data by a certain algorithm.

Figure 3:
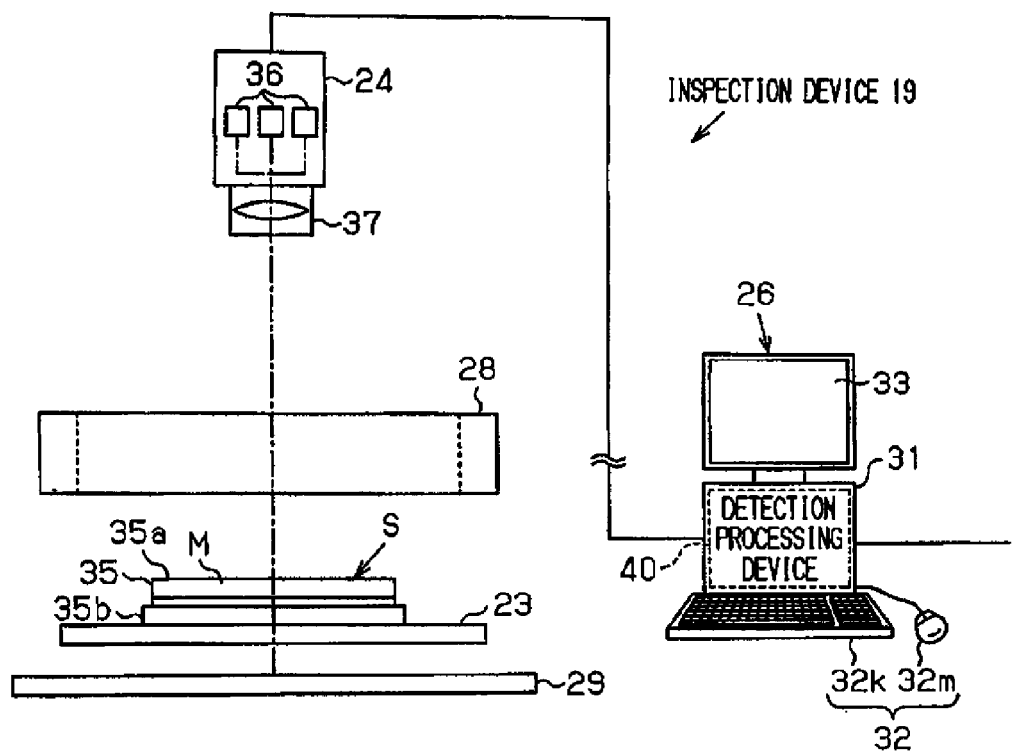
FIG. 3 is a schematic front view of the inspection device.

As shown in FIG. 3, the inspection device 19 includes the inspection bench 23, a circular light source 28, which illuminates a sample S on the inspection bench 23, a reflective plate 29, the camera 24, which captures an image of the sample S on the inspection bench 23, and a microorganism detection processing device (hereinafter simply referred to as "detection processing device 40"). The reflective plate 29 and the light source 28 are arranged on opposite sides of the inspection bench 23. The detection processing device 40 is built in a main body 31 of the personal computer 26, to which the camera 24 sends image data.

The inspection bench 23 is made of a light transparent material such as glass. The inspection bench 23 is supported to be movable by a supporting member, which is not shown in the drawing. The light source 28 is circular and is arranged between the camera 24 and the inspection bench 23. The central axis of the light source 28 corresponds to the optical axis of the camera 24. The camera 24 captures an image of the whole sample S on the inspection bench 23 through an opening of the light source 28. The reflective plate 29 is formed by, for example, a diffuser plate. The reflective plate 29 reflects light from the light source 28 as diffusion light. Therefore, the camera 24 can capture only an image of a sample S on the inspection bench 23.

A sample S is a petri dish 35 (e.g., glass petri dish) containing a medium M (agar medium and the like). The petri dish 35 including a lid 35*b* covering a dish 35*a* is inverted and placed on the inspection bench 23 so that the lid 35*b* faces toward opposite to the camera 24. This is to prevent contamination of the medium M with microorganisms in the constant temperature room 13 when the lid 35*b* is removed. Provided that the cleanliness in the constant temperature room 13 is sufficiently high, the lid 35*b* may be removed during inspection.

The dish 35*a* contains the medium M which contains an inspection subject, liquid beverage, at a certain proportion. The medium M in the petri dish 35 is cultivated in the constant temperature room 13 under predetermined temperature conditions for a predetermined cultivation period. The inspection device 19 inspects the petri dish 35 at the beginning of cultivation and multiple predetermined times during the cultivation period. When the transporting robot 20 repeatedly moves the petri dish 35 onto the inspection bench 23, the position of the petri dish 35 on the inspection bench 23 may shift from its original position by a few millimeters to about 1 cm and the angle of the petri dish 35 by a few degrees to about 30 degrees.

The camera 24 is a three chips color camera including three imaging elements 36 for R (Red), G (Green) and B (Blue). The imaging element 36 may be a CCD (Charge Coupled Device) image sensor or a CMOS image sensor or the like.

The camera 24 includes a lens unit 37 having an automatic focusing (autofocus) function and a zoom function. The camera 24 captures an image of a sample S (petri dish 35) on the inspection bench 23 at a predetermined magnification. Light incoming to the camera 24 through the lens unit 37 is separated into three primary colors of light RGB by a dichroic mirror or a dichroic prism, which is not shown in the drawing. The separated lights of RGB are respectively received at the respective imaging elements 36. The camera 24 may be a single chip color camera.

The personal computer 26 includes a main body 31, an input operation section 32 including a mouse 32*m* and a keyboard 32*k* and a monitor 33 (display). The camera 24 is connected to the main body 31. Analog signals generated from the respective imaging elements 36 in the camera 24 are A/D converted in the camera 24 and then sent to the main body 31 as RGB color image data. The detection processing device 40 in the main body 31 detects a microbial colony in the medium M based on color image data of the sample S delivered from the camera 24. The detection processing device 40 corresponds to the microorganism detecting device according to the present invention.

The main body 31 incorporates a microcomputer (hereinafter simply referred to as "computer 38") containing a CPU (central processing unit) and memory (e.g., RAM) (see FIG. 2). Memory in the main body 31 stores a program for a detection process of microorganisms installed from a memory medium such as a CD-ROM and the like. The computer 38 functions as the detection processing device 40, which executes the program read out from memory. A detection process for microorganisms by the detection processing device is described in detail hereinbelow.

Figure 2:
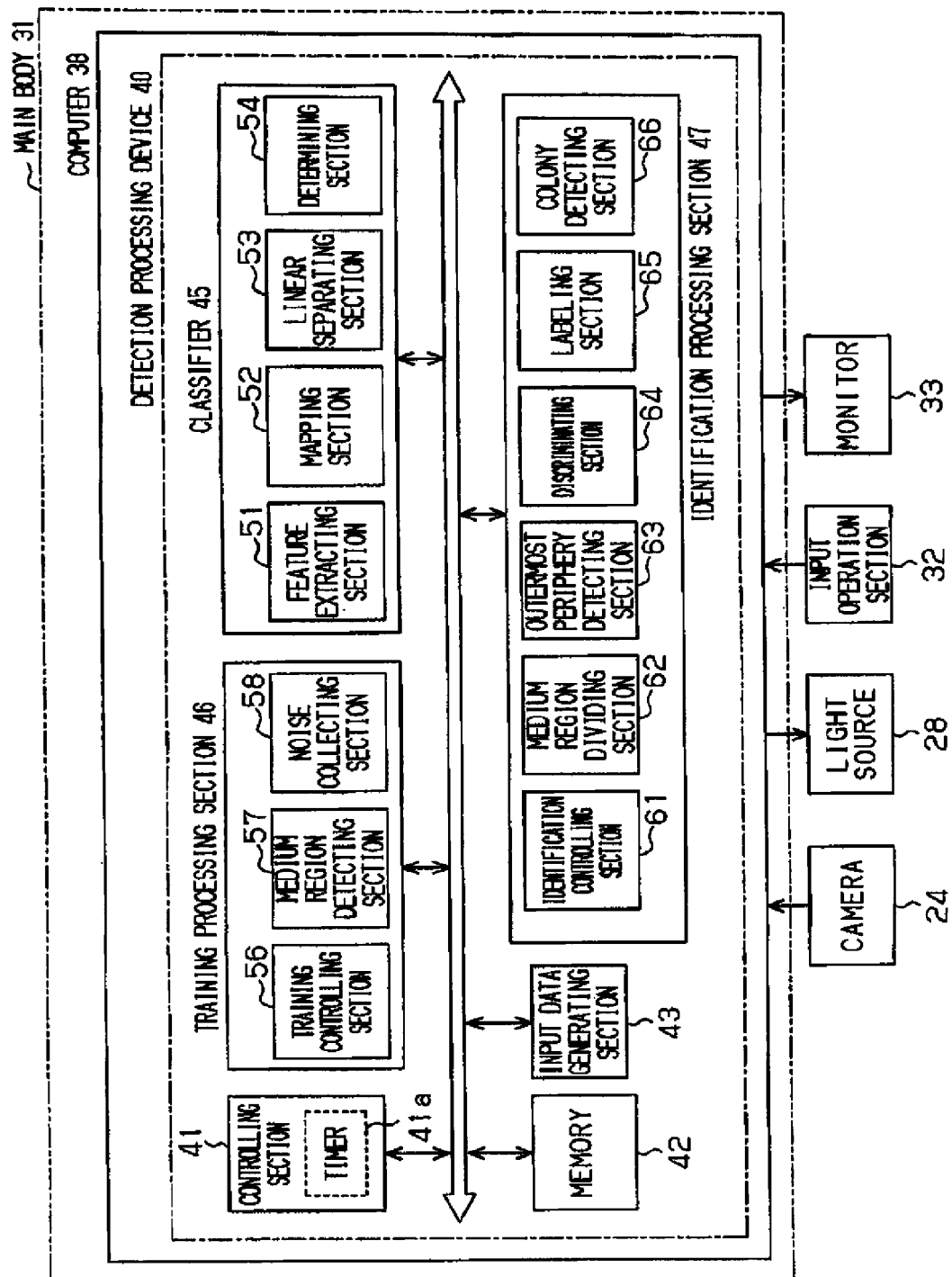
FIG. 2 is a block diagram showing electrical configuration of an inspection device.

As shown in FIG. 2, the computer 38 in the main body 31 is connected to the camera 24 and the light source 28. The computer 38 controls image capturing by the camera 24 (focus control, zoom control and the like) and illumination by the light source 28. The computer 38 is also connected to the input operation section 32 and the monitor 33. The computer 38 stores various setting data entered from the input operation section 32 in a memory 42 and displays images of the sample S or detection results of colonies on the monitor 33.

In FIG. 2, the respective function blocks shown in the detection processing device 40 are realized when the computer 38 runs the program for the detection process. The detection processing device 40 includes a controlling section 41, the memory 42, an input data generating section 43, a classifier 45, a training processing section 46, and a identification processing section 47.

The controlling section 41 controls the whole detection process and stores setting data in the memory 42. The controlling section 41 displays images of the sample S captured by the camera 24 and detection results of colonies on the monitor 33. The controlling section 41 displays a setting screen on the monitor 33. An operator operates the input operation section 32 to enter various setting data such as a cultivation period, a training period (learning period), a identification period (inspection period), a learning interval (learning sampling interval), a identification interval (identification sampling interval), the presence or absence of noise collection, a distance for threshold setting, the presence or absence of outermost periphery detection, the presence or absence of discrimination, colony identification conditions (area conditions or diameter conditions) and the like, thereby storing them in the memory 42. The memory 42 may be a partial memory area of a hard disk or RAM.

The controlling section 41 includes a timer 41*a*. The timer 41*a* measures the length of time from the start of cultivation to the end of the cultivation period. The cultivation period may be divided into a "training period", which is from the start of cultivation until a predetermined time, and an "identification period", which is after the predetermined period until the end of the cultivation period.

The cultivation period is defined according to varieties of detection subject microorganisms and is, for example, defined to be the range within 10 to 30 hours (e.g., 18 hours). The controlling section 41 understands, based on the time measured by the timer 41a, that it is in the training period or identification period, that learning or inspection sampling period has arrived, that the cultivation period has finished and the like.

The input data generating section 43 obtains input data to be supplied to the classifier 45 from color image data (input image) entered from the camera 24. Input data contains at least color data. Specifically, the input data generating section 43 obtains color data (RGB gradation values) for each of pixels within a defined range in color image data entered from the camera 24. Color data is provided as gradation values representing R, G and B with 256 gradations. The number of gradations of color data may be appropriately changed.

The classifier 45 is formed by at least one algorithm selected from a support vector machine (SVM) based on Kernel method, neural network (MLP: Multi-Layer Perceptron) and Gaussian mixture model (GMM). The classifier 45 includes two or three of SVM, MLP and GMM. An operator may manually choose SVM, MLP and/or GMM, or the detection processing device 40 may automatically choose the one suitable for a detection subject from SVM, MLP and GMM.

The classifier 45 includes a feature extracting section 51, a mapping section 52, a linear separating section 53 and a determining section 54 (identification section). The feature extracting section 51 is formed by at least one known function algorithm among SVM, MLP and GMM described above. The feature extracting section 51 carries out a feature extraction computing with input variables of input data from the input data generating section 43 by following the function algorithm, thereby feature vectors (feature vector data) x are formed. When color data (RGB gradation values) of pixels are used, the feature vectors x are represented by three-dimensional vectors containing feature vector components (xr, xg, xb) of three colors RGB. The feature vectors x may be a combination of RGB colors and color component data of at least a part of a color space other than a RGB color space (e.g., a HSV color space). In the following description, color data is assumed to be three-dimensional data of RGB gradation values.

The mapping section 52 is provided when the classifier 45 is support vector machine (SVM). The mapping section 52 maps input points x specified by the feature vectors sent from the feature extracting section 51 on a high-dimensional feature space according to a computing algorithm based on Kernel method. The mapping section 52 then forms high-dimensional feature vectors (high-dimensional feature vector data) and outputs output points (mapped points) $\psi(x)$ specified by the high-dimensional feature vectors. In the following description, the classifier 45 is assumed to be support vector machine (SVM) based on Kernel method.

Figure 4:
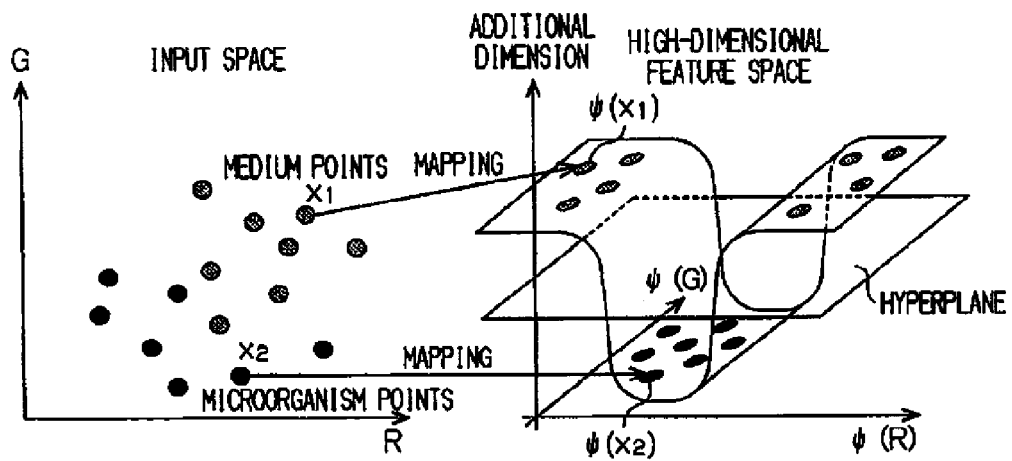
FIG. 4 is a graph depicting functions of a classifier.

FIG. 4 is a graph depicting mapping from an input space (feature space) onto a high-dimensional feature space. The left panel in FIG. 4 shows an input space containing input points x=(xr, xg, xb) specified by the feature vectors. The right panel in FIG. 4 shows a high-dimensional feature space containing output points (mapped points) $\psi(x)$ ($\psi(xr, xg, xb)$) specified by the high-dimensional feature vectors. In FIG. 4, for convenience of explanation of features of SVM, input points of medium x1 (medium points) and input points of microorganisms x2 (microorganism points) are shown in the input space. The input points x have three-dimensional data containing color feature amounts (xr, xg, xb). For convenience of explanation, the input space (feature space) is shown as a two-dimensional space with color feature amounts of two colors R and G on two coordinate axes in FIG. 4.

The three-dimensional input points x1 and x2 in the input space are mapped on the high-dimensional space to which an additional dimension is added by the mapping section 52 and output as output points $\psi(xr, xg, xb)$ specified by the high-dimensional feature vectors. The output points $\psi(xr, xg, xb, \ldots)$ are n-dimensional (n>3) feature vector data and contain n components ($\psi xr, \psi xg, \psi xb, \ldots$). (xr, xg, xb) and ($\psi xr, \psi xg, \psi xb, \ldots$) are coordinates of endpoints of the vectors.

In the input space shown in FIG. 4, the set of medium points x1 and the set of microorganism points x2 are not linearly separable. However, in the mapped high-dimensional feature space, a set of points $\psi(x1)$ mapped from the medium points x1 and a set of points $\psi(x2)$ mapped from the microorganism points x2 are linearly separable by a hyperplane specified by margin maximization. However, in the first embodiment, the input points x are only the medium points x1 and therefore only the class C1 of medium is classified by a hyperplane defined not by margin maximization but by a threshold which is a predetermined distance (distance for threshold setting $\Delta L$) outward from the set of points $\psi(x1)$ (see FIG. 6).

The linear separating section 53 linearly separates the set of points $\psi(x)$, which are either or both of the set of medium points $\psi(x1)$ and the set of microorganism points $\psi(x2)$ obtained during a training period, by a hyperplane (separation plane). The linear separating section 53 classifies at least one class C between the class C1 of medium and the class C2 of microorganisms.

Figure 6:
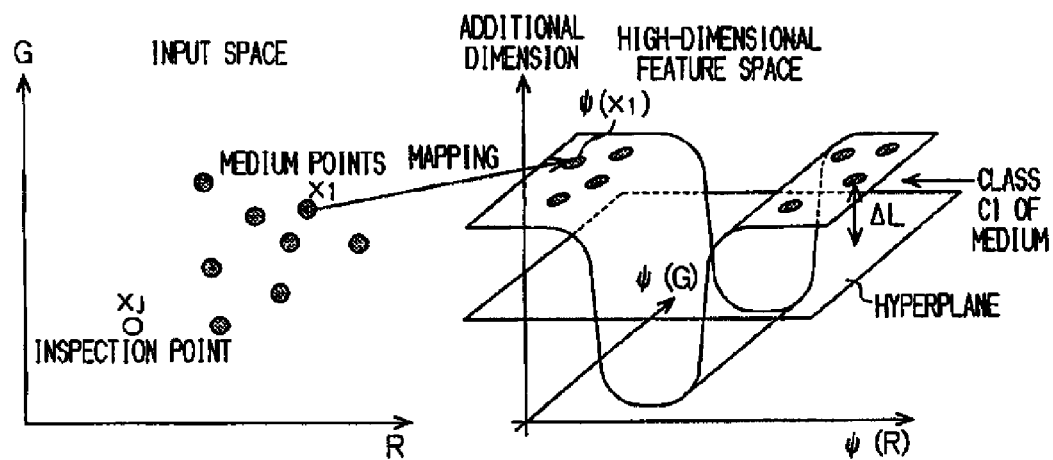
FIG. 6 is a graph depicting training of the classifier.

As shown in FIG. 6, in the present example in which the classifier 45 is trained with learning data of merely color data of the medium, the input points are only the medium points x1 shown in the input space and the set of medium points $\psi(x1)$ are only formed in the high-dimensional feature space to which the input points are mapped. The linear separating section 53 linearly separates the set of points $\psi(x1)$ by a hyperplane and color-classifies only the class C1 of medium. The memory 42 stores data for the distance for threshold setting $\Delta L$ as setting data for defining the hyperplane when only one class is classified. The linear separating section 53 sets a threshold at the position which is distant outward from the outermost point among the set of points $\psi(x1)$ (e.g., multiple points serving as support vectors) by $\Delta L$. Accordingly, the hyperplane shown in FIG. 6 is defined and the linear separating section 53 thus color-classifies the class C1 of medium. When only one class is classified, the classifier 45 is formed by at least one of support vector machine (SVM) based on Kernel method and Gaussian mixture model (GMM).

The determining section 54 (identification section) shown in FIG. 2 is used in order to identify the class to which inspection points belong during the identification period. The training processing section 46 shown in FIG. 2 includes, as necessary configurations for training of the classifier 45, a training controlling section 56, a medium region detecting section 57 and a noise collecting section 58. The training controlling section 56 provides setting data necessary for training and various instructions to the classifier 45 and provides instructions necessary for training to the medium region detecting section 57 and the noise collecting section 58. The training means is formed by the training processing section 46 and the classifier 45.

An image of a sample S captured by the camera 24 is now described. FIGS. 5(a) to 5(d) show images of a sample captured by the camera 24 during the cultivation period. FIG. 5(a) shows an image during training, FIG. 5(b) an image at initiation of identification, FIG. 5(c) an image when colonies are produced during identification and FIG. 5(d) an image displayed on the monitor 33 obtained by superimposing the captured image from the camera on a detection result of colonies. The medium M exemplified in FIG. 5(a) contains noise N which is an insoluble solid component in the inspection subject, liquid beverage. When the inspection subject is liquid beverage containing fruit, for example, small solids contained therein such as fruit skin, fruit pulp, fibers, seeds and the like may be noise N which induces false detection of colonies.

The medium region detecting section 57 detects a region in the medium M (hereinafter referred to as "medium region MA") within the image of the sample and also detects a training local region TA within the medium region MA (see FIG. 5(a)). The training local region TA is a training subject region, which is used by the classifier 45 to learn the color of the medium M. In the present example, in order to reduce the load of the training process, a partial region of the medium region MA is selected as the training local region TA. Specifically, the medium region detecting section 57 separates a region in the petri dish 35 from the medium region MA by image processing and further detects a local region without noise N within the medium region MA, which is then set as the training local region TA. By utilizing the difference in color between the noise N and the medium M, a boundary between regions having different color is detected as a color edge. An operator may manually set the training local region TA by operating the input operation section 32. The number and shape of the training local region TA may be appropriately selected.

The noise collecting section 58 collects noise data. Noise data are used for position discrimination, in which noise and a colony are discriminated based on their positions. The noise collecting section 58 detects noise N during the training period by using color edge detection or with the classifier 45. The noise collecting section 58 then collects noise data containing positions of detected noise N. For example, when the classifier 45 is used, the class C1 of medium is classified after at least one training on the training local region TA and the noise collecting section 58 then enters input data for each pixel within the medium region MA to the classifier 45 and identify noise points that do not belong to the class C1 of medium among the set of points x or the set of points $\psi(x)$ obtained as output points. The noise collecting section 58 then obtains a noise region that is a closed region containing a series of noise points and carries out computing on the positions in the noise region to obtain noise data. Noise data may contain the area and the gray value of the noise region.

The identification processing section 47 determines during the identification period whether or not the inspection point xj formed by the feature extracting section 51 based on input data of the respective points on the medium M (in case of GMM) or the mapped point $\psi(xj)$ obtained by mapping the inspection point xj by the mapping section 52 (in case of SVM) belongs to the class. The identification processing section 47 identifies, based on the result of the determination, whether the inspection point xj is the medium point or the microorganism point. The identification processing section 47 further extracts a closed region which contains a series of points (pixels) identified as the microorganism points. The identification processing section 47 then identifies whether or not the closed region is colonies of microorganisms in view of various determination conditions. In order to carry out such a identification process, the identification processing section 47 includes a identification controlling section 61, a medium region dividing section 62, an outermost periphery detecting section 63, a discriminating section 64, a labeling section 65 and a colony detecting section 66. The identification means is formed by the identification processing section 47 and the classifier 45, which has been trained (after learning).

The identification controlling section 61 provides instructions to the classifier 45 and each of the sections 62 to 66 when the identification process is performed. The medium region dividing section 62 is initiated when the setting is "with" outermost periphery detection. In this case, the medium region dividing section 62 divides, as shown in FIG. 5(b), the medium region MA in the image into a central main region A1 (central region) and an outermost periphery local region A2 (peripheral region). The central region may partially overlap with the peripheral region.

When the time measured by the timer 41a is within the training period, the controlling section 41 initiates the training processing section 46 to train the classifier 45.

When the time measured is within the identification period (inspection period), the controlling section 41 initiates the identification processing section 47 and carries out inspection with the classifier 45 after training.

In the present embodiment, a microbial detection process using the classifier 45 is performed on the main region A1. A feature extraction process in the classifier 45 is performed by the feature extracting section 51 according to the algorithm similar to that used during training. Namely, input data of all pixels within the main region A1 in image data from the camera 24 are sequentially entered for pixel by pixel from the input data generating section 43 to the classifier 45. The feature extracting section 51 forms a feature vector xj (inspection point) based on input data according to an algorithm. When the classifier 45 is SVM, the mapping section 52 maps the inspection point xj specified by the feature vector on the high-dimensional feature space to form a high-dimensional feature vector $\psi(xj)$. The determining section 54 in the classifier 45 then determines whether or not the point xj or point $\psi(xj)$ specified by the feature vector belongs to the class C (class C1 of medium in the present embodiment) classified by the classifier 45 during training and determines, based on the result of the determination, whether the inspection point xj is the medium point or the microorganism point.

Figure 7:
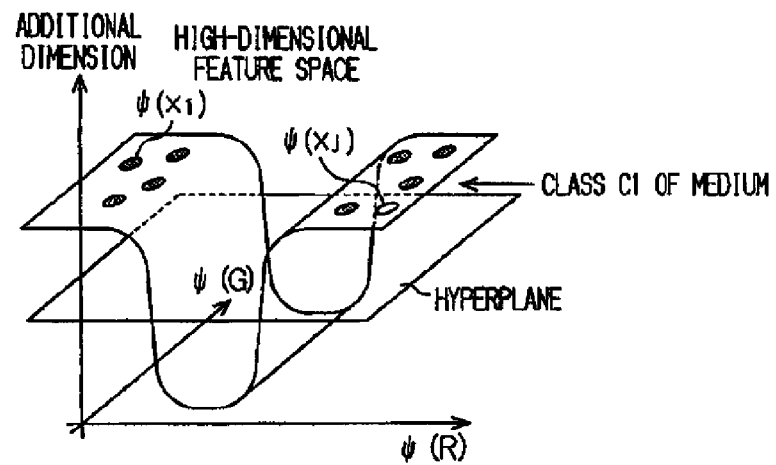
FIGS. 7(a) and 7(b) are graphs depicting identification of microorganisms by the classifier.
Figure 7:
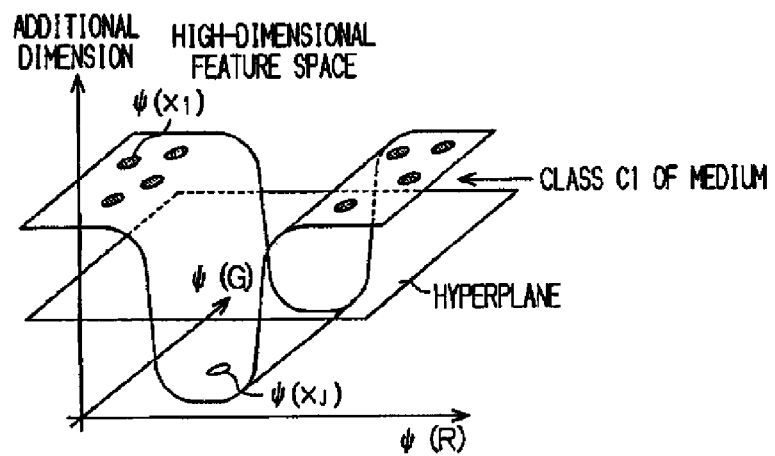

FIG. 7 is an example when the classifier is SVM and is a graph depicting the determination method by the determining section 54. The determining section 54 determines, as shown in FIG. 7(a), when the point $\psi(xj)$ (j=1, 2, ... ) mapped on the high-dimensional feature space belongs to the class C1 of medium, that the inspection point xj is the medium point. On the other hand, as shown in FIG. 7(b), when the point $\psi(xj)$ does not belong to the class C1 of medium, the determining section 54 determines that the inspection point xj is the microorganism point. At this stage, the microorganism point may possibly noise.

The outermost periphery detecting section 63 shown in FIG. 2 carries out microbial detection in the outermost periphery local region A2 by using a method different from that used for the main region A1. This is because the circular region in the vicinity of the outermost periphery of the medium region MA corresponds to the region in which, for example, the color of the medium M is affected by light refracted at a side wall of the petri dish 35 or by shadow of the side wall. Therefore, the outermost periphery detecting section 63 performs color edge detection in order to detect a boundary (color edge) between the regions having different colors within the outermost periphery local region A2. The outermost periphery detecting section 63 then carries out morphological operation on the region surrounded by the color edge and colony candidates are obtained whose shape is specified thereby.

The discriminating section 64 is initiated when the setting is "with" discrimination. The discriminating section 64 carries out shape discrimination, color discrimination and position discrimination in order to discriminate colonies other than noise N among detected objects (colony candidates) determined as the closed region which contains a series of microorganism points detected in the main region A1 and detected objects (colony candidates) detected in the outermost periphery local region A2. According to shape discrimination, it is determined whether features of the detected objects obtained by feature extraction and the like such as the area, the degree of circularity, convexity, minimum circumscribed circle and the like fulfill the shape conditions for colonies, which has been set or learned in advance. The discriminating section 64 discriminates detection objects which fulfill the above shape conditions as colonies. According to color discrimination, the degree of certain chromaticity is calculated respectively for the detected objects and the medium region and it is determined whether or not the difference in the degree of chromaticity therebetween is at or higher than a predetermined threshold.

The discriminating section 64 discriminates detected objects having the difference in the degree of chromaticity at or higher than the threshold as colonies. Color discrimination is performed on the detected objects pixel by pixel.

According to position discrimination, colonies are discriminated by comparing the positions of noise based on noise data collected in the training step with the positions of the detected objects. When the detected objects overlap with noise to make discrimination difficult in position discrimination, the area and gray value of the detected objects are used to perform position discrimination.

The labeling section 65 performs labeling operation, in which objects detected or discriminated as colonies in the main region A1 and the outermost periphery local region A2 are labeled. The detected objects that are detected or discriminated as not corresponding to noise N are labeled but the detected objects detected or determined as noise N are not labeled.

The colony detecting section 66 determines whether or not the area of the labeled detected objects fulfills predetermined area conditions and detects the detected objects fulfilling the area conditions as colonies. For example, when the area Sd of detected objects fulfills the area conditions defined with a lower limit $S_{lower}$ and an upper limit $S_{upper}$, $S_{lower} \leq Sd \leq S_{upper}$, the detected objects are detected as colonies. The area conditions may be either one of a lower limit or upper limit.

The controlling section 41 displays the detection result of colonies obtained from the identification processing section 47 on the monitor 33. When no colony is detected, detected number of colonies is displayed as "0".

When any colonies are detected, the detected number of colonies is displayed. In addition, as shown in FIG. 5(d), a mark 70 surrounding the detected colony is superimposed on the image of the medium M.

Figure 9:
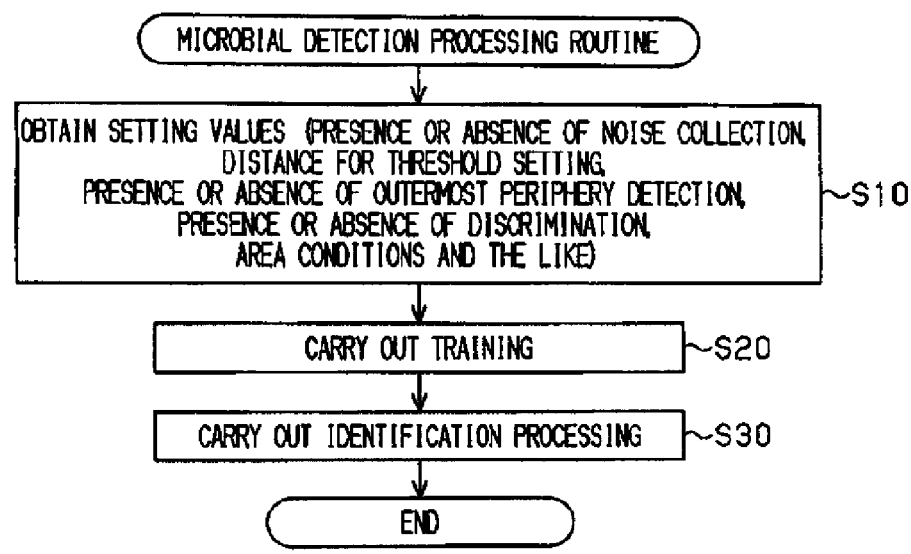
FIG. 9 is a flowchart showing a microbial detection processing routine.
Figure 10:
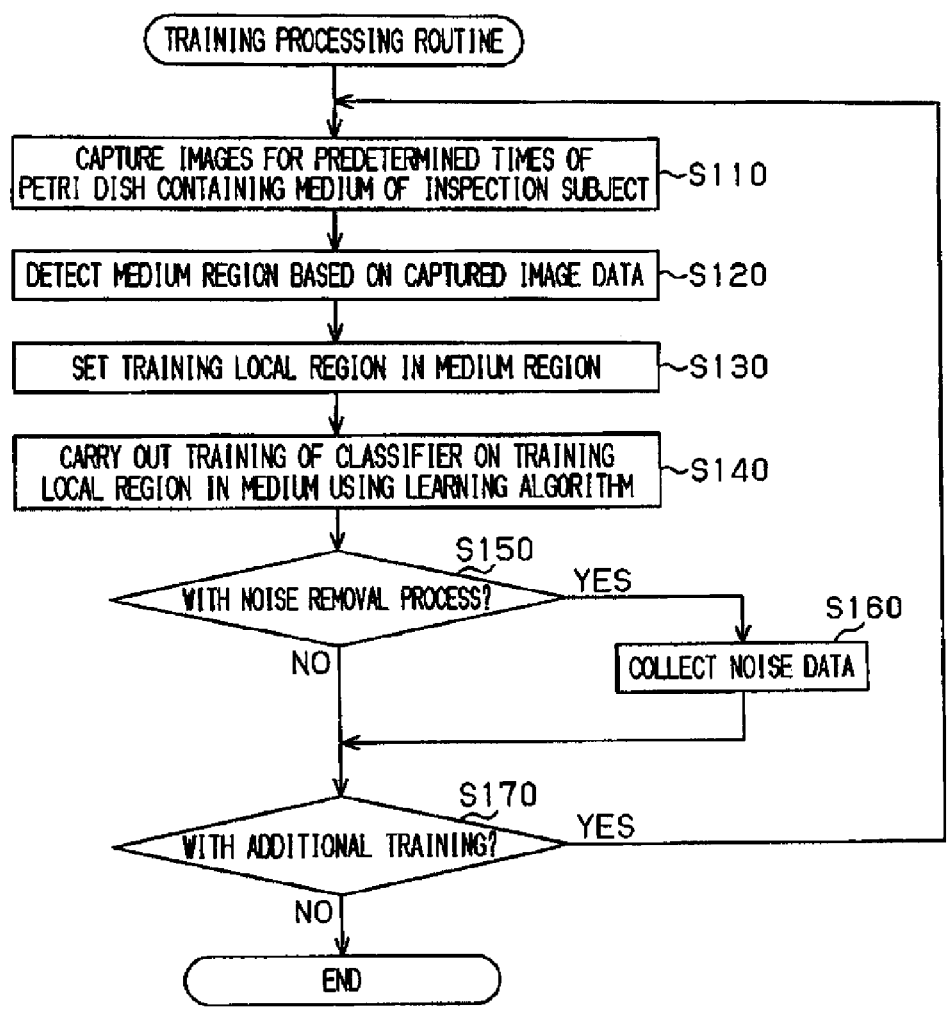
FIG. 10 is a flowchart showing a training processing routine.
Figure 11:
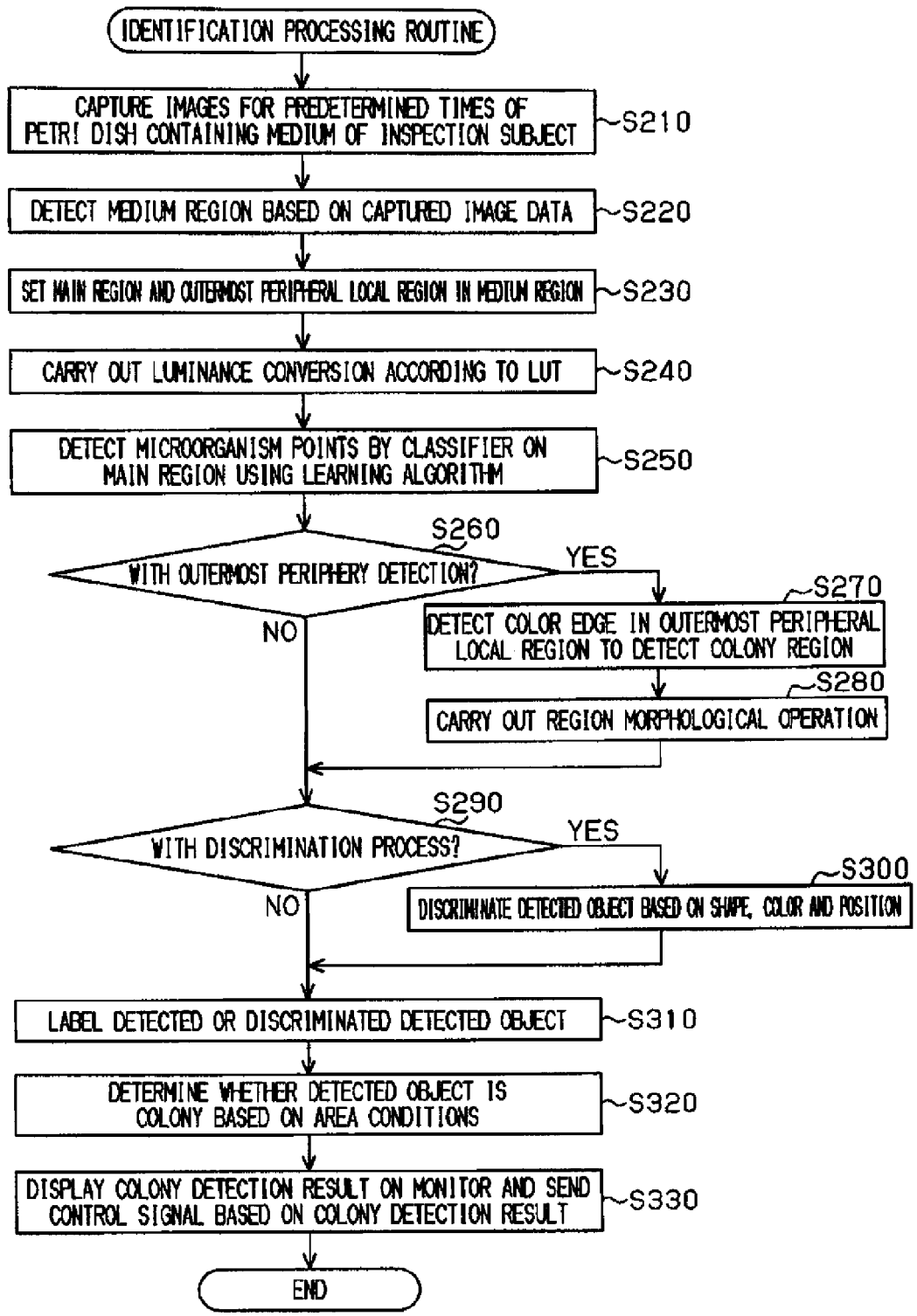
FIG. 11 is a flowchart showing an identification processing routine.

A microorganism detection process in the computer 38 is now described by referring to the flowcharts in FIGS. 9 to 11. The microorganism detection process is carried out by the detection processing device 40 shown in FIG. 2 with software.

As shown in FIG. 9, an operator first enters before the start of cultivation, by operating the input operation section 32, setting values such as the presence or absence of noise collection, the distance for threshold setting, the presence or absence of outermost periphery detection, the presence or absence of discrimination, area conditions and the like on the personal computer 26. The various setting values entered are stored in the memory 42. When an operator initiates inspection by using the input operation section 32, the computer 38 (detection processing device 40) initiates microorganism detection process.

In step S10, the computer 38 reads out from the memory 42 the setting values such as the presence or absence of noise collection, the distance for threshold setting, the presence or absence of outermost periphery detection, the presence or absence of discrimination, the area conditions and the like.

In step S20, the computer 38, during the training period, allows the classifier 45 to learn at least the color of the medium by using the image of the medium M captured by the camera 24. A training process in step S20 corresponds to the training step.

In step S30, the computer 38 performs, during the identification period, an identification process in order to identify the presence or absence of a microbial colony in the medium region. The identification process in step S30 corresponds to the identifying step.

The computer 38 performs a training processing routine shown in FIG. 10 in the training process of S20 and an identification processing routine shown in FIG. 11 in the identification process of S30. The training process and identification process are described in detail by following the flowcharts in FIGS. 10 and 11, respectively. The training processing section 46 performs the training process based on image data captured by the camera 24 using the input data generating section 43 and the classifier 45.

In step S110 in FIG. 10, one to ten, for example five images of the petri dish 35 containing the inspection subject, which is medium M, are taken by the camera 24.

In step S120, the medium region MA is detected based on the captured image data (see FIG. 5(a)).

In step S130, the training local region TA is set in the medium region MA (see FIG. 5(a)). For example, a region without noise N after searching noise N in the medium region MA is set as the training local region TA.

In step S140, the classifier 45 is trained on the training local region TA using a learning algorithm.

Specifically, the input data generating section 43 shown in FIG. 2 generates input data containing color data for each pixel within the training local region TA. The input data generating section 43 then serially sends input data as learning data to the classifier 45. The feature extracting section 51 in the classifier 45 forms, based on input data, feature vectors x1 according to the algorithm. When the classifier 45 is SVM, as shown in FIG. 6, the medium points x1 specified by the feature vectors are serially mapped on the high-dimensional feature space by the mapping section 52.

A set of points ψ(x1) is thus obtained, which is specified by the mapped high-dimensional feature vectors. A threshold is set as a hyperplane at a position which is distant outward from the set of points ψ(x1) by the distance for threshold setting ΔL. The hyperplane linearly separates the high-dimensional feature space and the class C1 of medium is classified by color.

In step S150, the presence or absence of noise collection is determined. When the setting is "with" noise collection, the process proceeds to step S160 and when the setting is "without" noise collection, proceeds to step S170.

In step S160, noise data are collected. The noise collecting section 58 detects color edges within the medium region MA and detects a region having a hue different from that of the medium M among color edges as noise N. The noise collecting section 58 calculates the position of the detected noise N, generates noise data containing at least the position data and stores it in the memory 42.

In step S170, the presence or absence of additional training is determined. During the training period, training may be performed as many times as desired and additional training can add learning data. A period during which addition of learning data is allowed (predetermined time) may be any appropriate value before microorganisms are produced. When additional training is carried out, the process returns to S110 and the sample S is again transported to the inspection bench 23 at the next time training is carried out after the learning sampling interval. The process in S110 to S170 is then similarly carried out with image data of the sample S captured by the camera 24. When there is no additional training, the training processing routine is completed.

The training process is carried out during the training period, which is from the start of cultivation (time 0) until a predetermined time (e.g., 5 hours) at learning sampling intervals (e.g., every 30 minutes or 1 hour). Due to this training, the classifier 45 classifies the class C1 of medium. In order to do this, for example, change in the color of the medium M is learned during the training period. In addition, data on deposits (ferric oxide or the like) generated due to oxidation of metal components in the liquid beverage such as emulsified iron are also collected as noise N.

When the time measured by the timer 41$a$ is after the predetermined time (e.g., 5 hours), the process shifts from the training period to the identification period. The computer 38 then initiates the identification processing routine shown in FIG. 11, wherein the identification processing section 47 performs the identification process using the input data generating section 43 and the classifier 45.

As shown in FIG. 11, in step S210, the camera 24 captures the same number of images as the images captured during training of the petri dish 35 containing the inspection subject, medium M.

In the next step S220, the medium region MA is detected based on the captured image data.

In step S230, the main region A1 and the outermost periphery local region A2 are set within the medium region MA.

In step S240, luminance conversion is performed according to a lookup table (LUT). In luminance conversion, contrast adjustment, gamma correction and the like are carried out.

Figure 5:
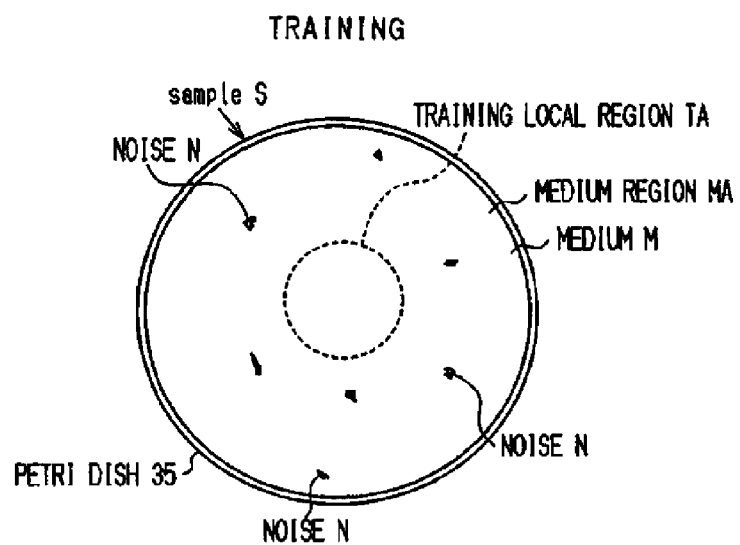
FIGS. 5(a) to 5(d) are schematic diagrams showing samples in different stages.
Figure 5:
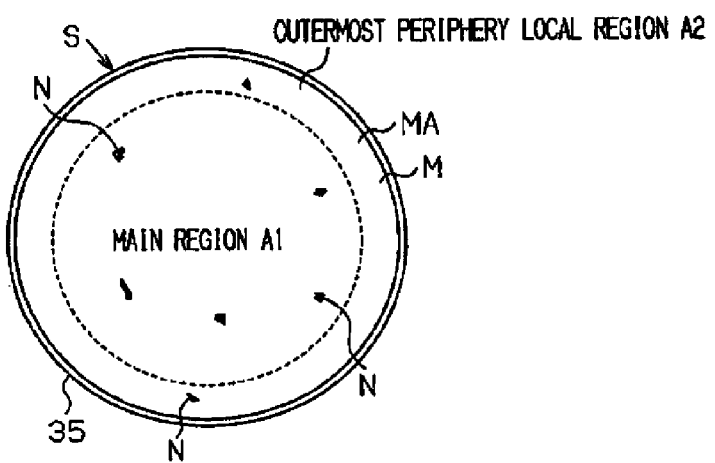
Figure 5:
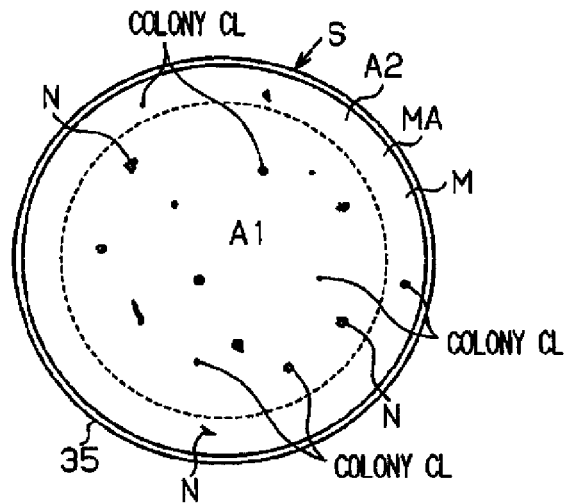
Figure 5:
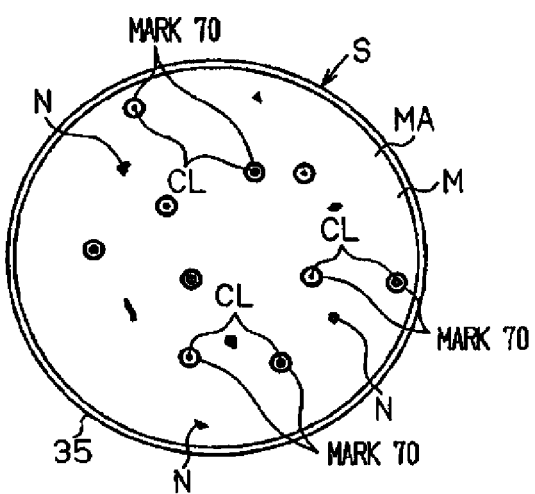

In the next step S250, the microorganism points are detected from the main region A1 by the classifier 45 using the learning algorithm. Specifically, the input data generating section 43 shown in FIG. 2 generates input data containing color data for each pixel within the main region A1, which are then serially sent to the classifier 45. The feature extracting section 51 in the classifier 45 forms, based on input data, the feature vectors $x_j$ ($j=1, 2, \ldots$) (inspection points). When the classifier 45 is SVM, the inspection points $x_j$ specified by the feature vectors shown in FIG. 6 are serially mapped on the high-dimensional feature space by the mapping section 52. The mapped points $\psi(x_j)$ are then obtained which are specified by high-dimensional feature vectors (see FIG. 7). As shown in FIG. 7($a$), when the mapped points $\psi(x_j)$ belong to the class C1 of medium, the inspection points $x_j$ are determined (identified) as the medium points. On the other hand, as shown in FIG. 7($b$), when the mapped points $\psi(x_j)$ do not belong to the class C1 of medium, the inspection points $x_j$ are determined (identified) as the microorganism points. As shown in FIG. 5($c$), at 3 to 5 hours after entering the identification step, for example, colonies CL may be produced. In this case, the points $\psi(x_j)$ obtained by mapping the inspection points $x_j$ based on input data of pixels in the colonies CL (in case of SVM) do not belong to the class C1 of medium as shown in FIG. 7($b$) and are detected as the microorganism points. Such a detection process is performed for all pixels in the main region A1.

In step S260, the presence or absence of outermost periphery detection is determined. When the setting is "with" outermost periphery detection, the process proceeds to step S270 and when the setting is "without" outermost periphery detection, the process proceeds to step S290.

In step S270, color edges are detected in the outermost periphery local region A2 and the colony region is detected based on the difference in hue from the medium. The colony region is a region of detected objects (colony candidates) that may possibly be a noise region.

In the following step S280, the shape of the detected objects is adjusted to, for example, a circular shape or an elliptical shape by region morphological operation.

In step S290, the presence or absence of a discriminating process is determined. When the setting is "with" the discriminating process, the process proceeds to step S300 and when the setting is "without" the discriminating process, the process proceeds to step S310.

In step S300, the detected objects are discriminated based on the shape, color and position. The detection results for the main region A1 and the outermost periphery local region A2 are integrated. On the integrated result, feature extraction is carried out for the closed region containing a series of the microorganism points and the detected objects (colony candidates) are detected. According to shape discrimination, the area, the degree of circularity, convexity, minimum circumscribed circle and the like of the detected objects are computed. The detected objects having the feature amounts extracted that fulfill the shape conditions of colonies are discriminated as colony candidates. According to color discrimination, the degree of certain chromaticity is calculated respectively for the detected objects and the medium region. The detected objects having the difference in the degree of chromaticity between the detected objects and the medium region at or higher than a predetermined threshold are discriminated as colony candidates. According to position discrimination, the position of noise determined from noise data read out from the memory 42 and the computed positions of the detected objects are compared. The detected objects that do not overlap with noise are discriminated as colony candidates. When the detected objects overlap with noise to make discrimination difficult in position discrimination, the area and gray value of the detected objects are used to discriminate the colony candidates. According to the discrimination step, noise N and the like among the detected objects is not discriminated as a colony, so that the detected objects (colony candidates) are further narrowed down.

In step S310, the detected objects that have been detected or discriminated are labeled. Namely, the detection results for the main region A1 and the outermost periphery local region A2 are integrated and all detected objects that have been detected or discriminated throughout the whole region of the medium region MA are labeled. When the discrimination process of S300 has been performed, the detected objects discriminated as noise in the discrimination process are excluded from labeling.

In step S320, it is determined whether or not the detected objects are colonies based on the area conditions. The colony detecting section 66 examines whether or not the area of the labeled detected objects fulfills the area conditions read out from the memory 42. When the area Sd of the detected objects fulfills the area conditions $S_{lower} \leq Sd \leq S_{upper}$, the detected objects are determined to be colonies CL.

In step S330, the detection result of colonies is displayed on the monitor 33 and a control signal according to the detection result of colonies is sent. Namely, when the detection result of colonies delivered from the identification processing section 47 is the detected number of "0", the controlling section 41 displays that the detected number of colonies is "0" on the monitor 33. On the other hand, when the detection result of colonies is the detected number of "N" (N≥1), the controlling section 41 displays the detected number of colonies of "N" on the monitor 33 and superimposes a mark 70 surrounding the detected colony CL on the image of the sample S displayed on the monitor 33 as shown in FIG. 5(d). If the mark 70 is displayed, an operator, who is looking at the monitor 33 outside of the constant temperature room 13, can easily understand the status of colony production in the sample S under inspection. The control signal from the controlling section 41 is sent to the controller 25. When the detected number of colonies is "N" (N≥1), the inspection is halted when the colony (colonies) is detected and the controlling section 41 sends the control signal to the controller 25 so that the sample S is discharged. As a result, the controller 25 controls the transporting robot 20 to transport the sample S determined as an inferior sample to the discharge shelf 17 and drives the conveyor 17a to discharge the sample S to the outside of the constant temperature room. On the other hand, when the detection result of colonies is the detected number of "0", the sample S is returned to the storage shelf 18. The sample S for which no colony is detected after the cultivation period is transported to the discharge shelf 16 for fair samples by the transporting robot 20 and discharged by the conveyor 16a to the outside of the constant temperature room.

Conventionally, inspection is carried out after the cultivation period, and production of beverages has to be halted for each lot for which at the most one colony is detected. According to the inspection device 19 of the present embodiment, a colony can be detected during the cultivation period and production of beverages can be halted at an early stage when a colony is detected. Therefore, the number of inferior products of beverages can be reduced as low as possible.

Figure 8:
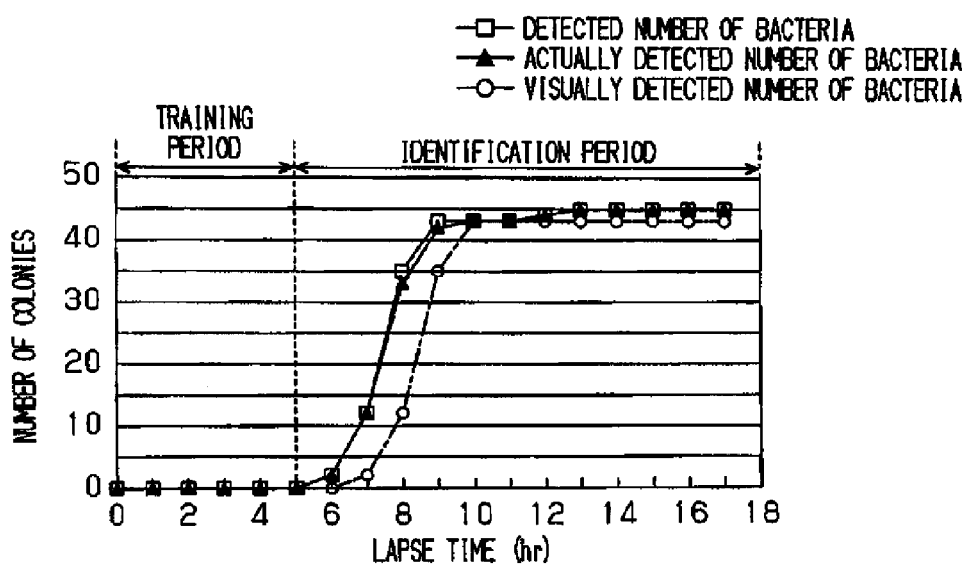
FIGS. 8(a) and 8(b) are graphs showing the number of bacteria detected by the detection processing device.
Figure 8:
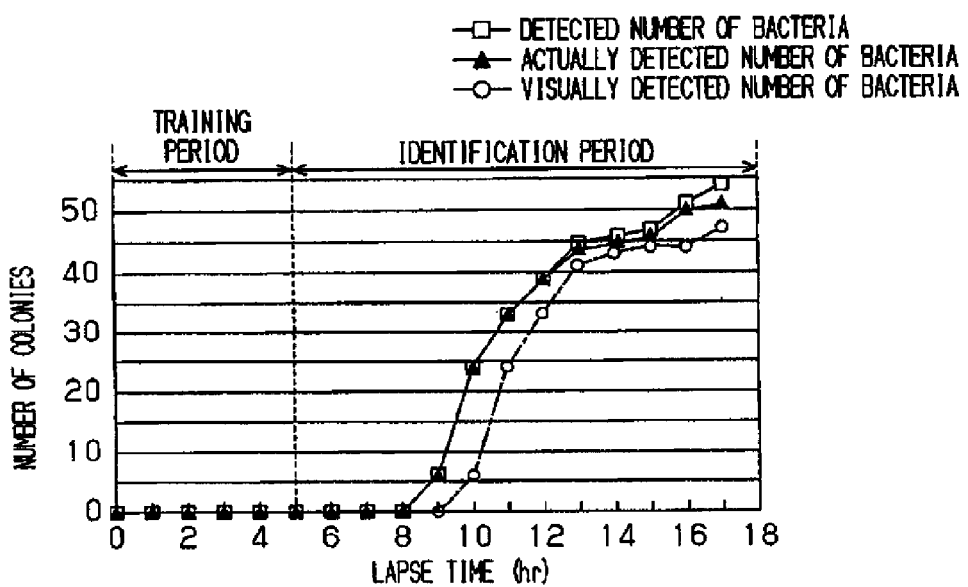

FIG. 8 shows graphs comparing the detected number of bacteria, the actually detected number of bacteria and the visually detected number of bacteria at inspection of a sample S with the inspection device 19. *Escherichia coli* was added to a medium M containing sample liquid beverage and cultivated for 18 hours. The horizontal axis represents the lapse time (hr) after the start of cultivation and the vertical axis represents the number of colonies. The samples S in FIGS. 8(a) and 8(b) have different colors in the media due to the difference in color of the inspection subject liquid beverage. In the graphs, the detected number of bacteria corresponds to the number of bacteria detected by the detection processing device 40 at regular time intervals. The actually detected number of bacteria corresponds to the actually measured value of the number of bacteria including very minute colonies at each time point in the cultivation period. The visually detected number of bacteria is the number of bacteria detected by visual inspection of the media by skilled inspectors at regular time intervals. In the examples shown in FIG. 8, the training period is from the start of cultivation until 5 hours and the identification period (inspection period) is after 5 hours. As can be seen from the graphs in FIGS. 8(a) and 8(b), the detected number of bacteria and the actually detected number of bacteria both continue to be "0" during the training period. At 6 to 8 hours after the start of cultivation, microorganisms begin to be detected. The shift of the detected number of bacteria is almost the same as the shift of the actually detected number of bacteria. This result shows that the bacteria detection by the detection processing device 40 has high accuracy without being affected by the color of media. During the identification period, the detected number of bacteria shifts as being higher than the visually detected number of bacteria. This result shows that the inspection device 19 allows detection of small colonies earlier than that being possible by visual inspection. The size of microbial colonies detectable by the inspection device 19 was the size which was almost undetectable by visual inspection, specifically about 0.008 square millimeters.

As described hereinabove in detail, the first embodiment provides the following advantages.

(1) It is determined whether or not the inspection point xj or the mapped point ψ(xj) specified by the feature vectors obtained by the classifier 45 based on input data containing color data belongs to the class C1 of medium classified by color in the training step (S20). Based on the result of the determination, it is identified whether or not the inspection point xj is a colony. Because of this, colonies can be precisely detected. For example, even when the medium M and colonies CL have similar colors, by using the classifier 45, which is SVM, the medium and colonies are linearly separable in the high-dimensional feature space, thereby allowing precise detection of colonies. Because of the nature of the method such that colonies are detected based on color feature, colonies are also precisely detected even when the position or angle of the petri dish 35 on the inspection bench 23 shifts between during training and identification from the original one, or the relative positions of the camera 24 and the petri dish 35 are changed.

(2) Even when the color of colonies varies depending on the species of microorganisms, e.g., the colonies of *E. coli* are reddish and those of yeasts are greenish, colonies of microorganisms (bacteria) can be precisely detected by using the same algorithm in the classifier 45.

(3) Deposits obtained by oxidation of metal components such as emulsified iron and the like may sometimes exhibit similar color as colonies. In the training step, learning data of noise N of deposits and the like produced after the start of cultivation are accumulated, and noise data of noise N of the deposits are collected. In this case, the inspection points for the deposits and the like are determined to belong to the class C1 of medium. Even if the inspection points are detected not to belong to the class C1 of medium but are detected as detected objects that may possibly be colonies, these inspection points are excluded from the detected objects as noise according to the shape, color and position thereof. Thus, it can be avoided that the deposits and the like are incorrectly detected as colonies, thereby allowing precise detection of colonies.

(4) In the training step, the inspection subject (sample S) is used as a learning subject and the training period is selected as a predetermined period before production of microbial colonies (from the start of cultivation until a certain time (as an example, 5 hours)). Because of this, even when the color of the medium M is changed during the training period, the resulting color is learned as the color of the medium M. Accordingly, even when the color of the medium is changed, colonies can be precisely detected. Even when the color of the medium varies depending on the inspection subjects due to the color of the inspection subject beverages, the color of the medium is learned for every inspection subject by training, thereby allowing precise detection of colonies.

(5) For a closed region that contains a series of microorganism points for which the inspection points xj or mapped points ψ(xj) are determined to not belong to the class C1 of medium, the detected objects that are detected or determined by feature extraction within the main region A1 and the detected objects that are detected or determined by color edge detection and region morphological operation within the outermost periphery local region A2 are integrated. The above detected objects are labeled and among these detected objects the ones fulfilling the area conditions are identified as colonies. Thus, detected objects that may possibly be noise are excluded, thereby allowing precise detection of colonies.

(6) In case of an inspection subject that contains noise N (foreign substances) such as fruit skin, colonies and noise are discriminated among the detected objects by shape discrimination, color discrimination and position discrimination in the discrimination step. Because of this, noise N is effectively prevented from being incorrectly detected as a colony. Therefore, cultured microbial colonies are accurately detected even in the medium containing fruit skin or fruit pulp having similar color as colonies.

(7) In the training step, only the medium is learned. Therefore, necessary process and operation are simple compared to the method in which learning on colonies is carried out. In the method wherein learning on colonies is carried out, an operator needs to specify colonies and enter and designate the regions of the specified colonies on the computer 38. In this respect, according to the method of the present embodiment, in which learning is carried out only on the medium M, such operation for specifying and entering colony regions is not necessary and the computer 38 can automatically learn.

(8) Inspection is carried out with the training period on a medium that is selected until a predetermined time (e.g., 5 hours) before production of microbial colonies and the identification period for identifying (detecting) microorganisms after the predetermined time. Since training can be carried out with the inspection subject, sample S, colony detection accuracy is improved. In a method in which learning on colonies is carried out, training cannot be carried out during the cultivation period of the inspection subject (sample S). Because of this, colony detection accuracy may be decreased because the training subject is different from the inspection subject. In addition, the training period is provided separately from the inspection period, thereby increasing the time required for training and identification. In this respect, according to the present embodiment, the period before production of colonies can be used for training, thereby reducing the time required for training and identification.

(9) A mark 70 surrounding a colony CL is superimposed on the image of the sample S displayed on the monitor 33. Because of this, the detected colonies are visually displayed and an operator can easily and visually confirm the status of colony production.

(10) It is required at manufacturing scenes of food products and the like to understand hygienic conditions of the processes and to ship the goods promptly. As described above, by employing the inspection device 19 of the present embodiment at the manufacturing scenes of food products and the like, colonies can be rapidly and accurately detected. Because of this, it can address understanding of hygienic conditions of the processes and prompt shipping of the goods. When microbial inspection is speeded up, inferior products can be avoided from shipping with judgment at early stages. Thus, it is very useful in terms of risk control.

Second Embodiment

Figure 12:
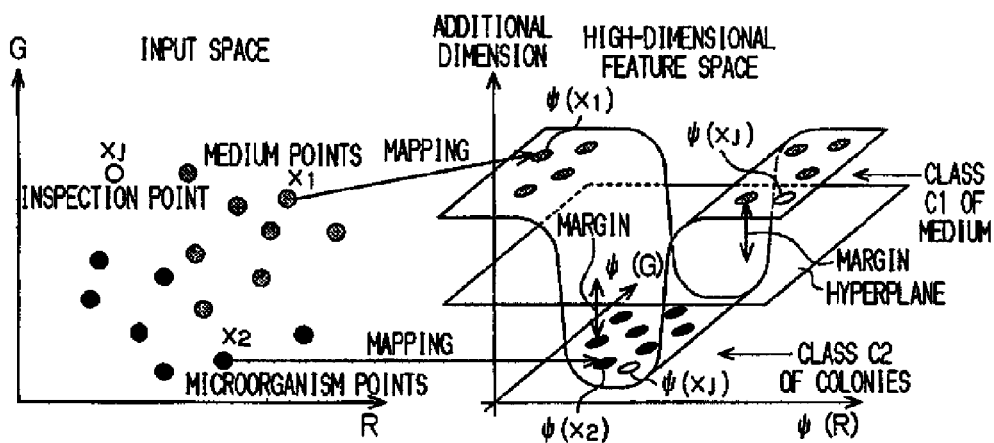
FIG. 12 is a graph depicting training and identification according to a second embodiment of the present invention.

The second embodiment is now described according to FIG. 12. The second embodiment is an example in which, in the training step (S20), training is carried out on both medium and microorganisms (colonies). The configurations of the inspection device 19 (FIGS. 1 and 3) and detection processing device 40 (FIG. 2) and substantial processing in the microbial detection processing routine (FIGS. 9 to 11) are basically the same as those in the first embodiment.

FIG. 12 depicts mapping from an input space to a high-dimensional feature space when the classifier is SVM. In FIG. 12, input points in medium x1 (medium points) and input points in colonies x2 (microorganism points) are shown in the input space. As shown in FIG. 12, the set of medium points ψ(x1) specified by the feature vectors obtained by mapping the medium points x1 on the high-dimensional feature space and the set of microorganism points ψ(x2) specified by the feature vectors obtained by mapping the input points x2 on the high-dimensional feature space are linearly separable.

The linear separating section 53 linearly separates the set of medium points ψ(x1) and the set of microorganism points ψ(x2) in the high-dimensional feature space by a hyperplane that is set at a position to maximize margin from the respective support vectors (closest point). Accordingly, the class C1 of medium and the class C2 of colonies (microorganisms) are classified.

In this case, training of the classifier 45 on the medium is carried out in the same manner as in the first embodiment. On the other hand, training of the classifier 45 on the colonies is carried out as follows. Namely, using a medium containing colonies of the same species, an operator designates a colony region through the input operation section 32 while looking at the medium M on the monitor 33. Training of the classifier 45 is carried out on the designated colony region. Training of the classifier 45 may be carried out on artificially prepared colonies. When more than one class is classified, the classifier 45 may be neural network (MLP) in addition to support vector machine (SVM) based on Kernel method and Gaussian mixture model (GMM).

In the identifying step (S30), as the first embodiment, the input data generating section 43 shown in FIG. 2 forms input data containing color data for each pixel in the main region A1. The input data generating section 43 then serially sends input data as learning data to the classifier 45. The feature extracting section 51 in the classifier 45 carries out a feature extraction computing according to a function algorithm using input data as input variables, thereby forming a feature vector xj (inspection point). When the classifier 45 is SVM, the mapping section 52 forms high-dimensional feature vector ψ(xj) by mapping the inspection point xj specified by the feature vector xj on the high-dimensional feature space shown in FIG. 12. The determining section 54 determines to which of the class C1 of medium or the class C2 of colonies the points ψ(xj) specified by the high-dimensional feature vector ψ(xj) belong, thereby detecting microorganism points. When the point ψ(xj) belongs to the class C2 of colonies, this point is detected as the microorganism point. FIGS. 10 and 11 are basically the same as the first embodiment except that the classifier 45 is trained on the medium and colonies (S140) and that the inspection point xj or the point ψ(xj) is detected as the microorganism point when it belongs to the class C2 of colonies (S250). When the classifier 45 is GMM or MLP, without mapping to the high-dimensional feature space, it is determined in S250 whether or not the inspection points xj formed by a feature extraction computing according to the function algorithm of GMM or MLP belong to the class of colonies.

According to the second embodiment, in addition to the advantages (1), (3), (5), (6), (9) and (10) in the first embodiment, the following advantages are obtained.

(11) In the training step, the class C1 of medium and the class C2 of colonies are classified, and the medium and colonies are identified from other. Because of this, determination as to whether the inspection point xj is the medium or the microorganism point can be more precisely carried out compared to the first embodiment. Thus colony detection accuracy is further improved.

(12) In the training step, when the classifier 45 is SVM, the mapping section 52 forms the set of medium points $\psi(x1)$ and the set of colony points $\psi(x2)$ in the high-dimensional feature space. The linear separating section 53 linearly separates the set of medium points $\psi(x1)$ and the set of colony points $\psi(x2)$ in the high-dimensional feature space by a hyperplane that maximizes margin (distance) from the respective support vectors. Because of this, the two classes C1 and C2 are appropriately classified by color. In the identifying step, it is determined whether or not the point $\psi(xj)$ of the high-dimensional feature vector obtained by mapping the inspection point xj belongs to the class C2 of colonies, thereby increasing identification accuracy of colonies in the identifying step.

Third Embodiment

A third embodiment will now be described by referring to FIG. 13. In the third embodiment, training only on microorganisms is carried out among the medium and microorganisms (colonies) in the training step. In this case, training is carried out in the same manner as in the second embodiment, in which the classifier 45 is trained on the colony region. The configurations of the inspection device 19 (FIGS. 1 and 3) and detection processing device 40 (FIG. 2) and substantial processing in the microbial detection processing routine (FIGS. 9 to 11) are basically the same as those in the first embodiment.

Figure 13:
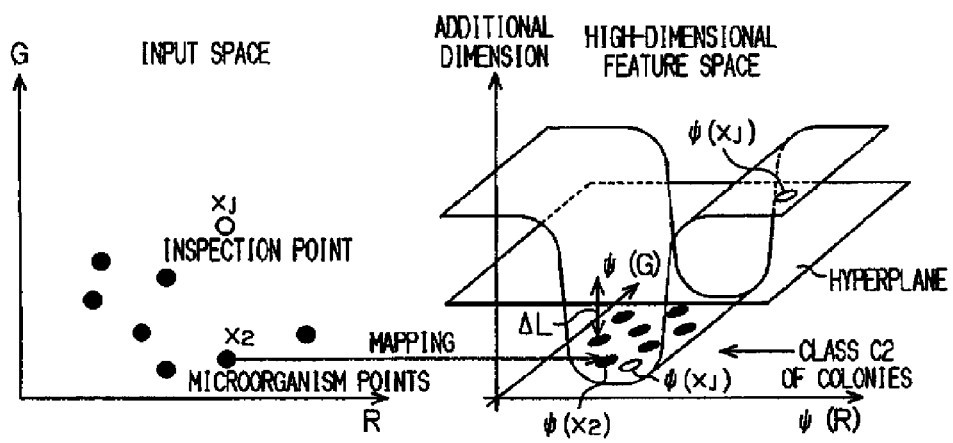
FIG. 13 is a graph depicting training and identification according to a third embodiment of the present invention.

FIG. 13 is a graph depicting mapping from an input space to a high-dimensional feature space when the classifier is SVM. In FIG. 13, input points in colonies x2 (microorganism points) are shown in the input space. As shown in FIG. 13, the microorganism points $\psi(x2)$ specified by the high-dimensional feature vectors obtained by mapping the microorganism points x2 on the high-dimensional feature space are linearly separated by a hyperplane that is distant outward from the set of points $\psi(x2)$ by a distance for threshold setting $\Delta L$, thereby classifying the class C2 of colonies. When one class is classified, the classifier 45 is formed by at least one of support vector machine (SVM) based on Kernel method and Gaussian mixture model (GMM).

In the identifying step (S30), as the first embodiment, the input data generating section 43 shown in FIG. 2 forms input data containing color data for each pixel in the main region A1. The input data generating section 43 then serially sends input data as learning data to the classifier 45. The feature extracting section 51 in the classifier 45 carries out a feature extraction computing according to a function algorithm using input data as input variables, thereby forming the feature vector xj (inspection point). When the classifier 45 is SVM, the mapping section 52 forms high-dimensional feature vector $\psi(xj)$ by mapping the inspection point xj specified by the feature vector xj on the high-dimensional feature space shown in FIG. 13. The determining section 54 determines whether or not the point $\psi(xj)$ specified by the high-dimensional feature vector $\psi(xj)$ belongs to the class C2 of colonies. When the point $\psi(xj)$ belongs to the class C2 of colonies, the point $\psi(xj)$ is detected as the microorganism point. FIGS. 10 and 11 are basically the same as the first embodiment except that the classifier 45 is trained on colonies (S140) and that when the inspection point xj or the point $\psi(xj)$ belongs to the class C2 of colonies, this point is detected as the microorganism point (S250). When the classifier 45 is GMM, without mapping to the high-dimensional feature space, it is determined (identified) in S250 whether or not the inspection point xj formed by a feature extraction computing according to the function algorithm of GMM belongs to the class of colonies.

According to the third embodiment, in addition to the advantages (1), (3), (5), (6), (9) and (10) in the first embodiment, the following advantages are obtained.

(13) Since the class C2 of colonies is classified in the training step, determination on whether or not the inspection point xj is the microorganism point can be more precisely carried out compared to the first embodiment. Thus colony detection accuracy is further improved.

(14) Since change in the color of colonies can be learned in the training step in advance throughout the cultivation period by cultivating the sample S, which is a learning subject, colonies are precisely identified even when the color of colonies produced in the sample S, which is an inspection subject, is changed with time in the identifying step.

Fourth Embodiment

In the above embodiments, input data for the classifier is color data. In the present embodiment, shape data is added to color data. For example, colonies of bacteria (E. coli and the like) have an approximate circular shape such as circular and elliptical, so that they can be distinguished from the shape of noise (foreign substances) such as fruit skin or deposits. An example of modification may include the second embodiment in which, in addition to color data of the respective medium and colonies, shape data of the colonies are sent to the classifier 45 as input data. Another example of modification may include the third embodiment in which, in addition to color data of colonies, shape data of the colonies are sent to the classifier 45 as input data. In the former case, the classifier 45 may be SVM, MLP and GMM and in the latter case, the classifier 45 may be SVM and GMM.

In the training step, an operator specifies colonies by carrying out input operation or by image processing based on a color image of the medium M containing colonies. The shape of the region identified as colonies is normalized to obtain shape data. Input data containing color data and shape data of colonies are sent from the input data generating section 43 to the classifier 45 as learning data. The feature extracting section 51 in the classifier 45 carries out a feature extraction computing according to a function algorithm using input data as input variables, thereby forming the feature vectors x2=(xr, xg, xb, xshape) (microorganism points). When the classifier 45 is SVM, the mapping section 52 obtains the high-dimensional feature vectors $\psi(x2)$ by mapping the microorganism points x2 specified by the feature vectors on the high-dimensional feature space. The linear separating section 53 defines a threshold as a hyperplane at the position distant outward from the set of points x2 of feature vectors (in cases of MLP and GMM) or the set of points $\psi(x2)$ of the high-dimensional feature vectors (in case of SVM) by a distance for threshold setting $\Delta L$ (predetermined distance). The hyperplane allows classification of the class C2 of colonies based on the features of color and shape.

In the identifying step, the medium and others (foreign substances, colonies and the like) are distinguished based on color by image processing. A computation is carried out on the shape of the regions other than the medium and the computed shape is normalized to obtain shape data. Color data of the regions other than the medium are obtained by averaging the color of pixels in the regions. The input data generating section 43 forms input data containing color data and shape data for each region. The input data generating section 43 sends input data as learning data to the classifier 45. The feature extracting section 51 in the classifier 45 carries out a feature extraction computing according to a function algorithm using input data as input variables to form the feature vector xj=(xr, xg, xb, xshape) (inspection point).

When the classifier 45 is SVM, the mapping section 52 forms the high-dimensional feature vector $\psi(xj)$ by mapping the inspection point xj specified by the feature vector xj on the high-dimensional feature space. It is then determined whether or not the point xj or the point $\psi(xj)$ belongs to the class C2 of colonies by comparing the point xj specified by the feature vector xj with a threshold (in cases of MLP and GMM) or by comparing the point $\psi(xj)$ specified by the high-dimensional feature vector $\psi(xj)$ with a threshold (in case of SVM). When the point xj or the point $\psi(xj)$ belongs to the class C2, it is identified that the inspection point xj is a colony.

In the above method, feature vectors of color data and shape data are formed on a common feature space. However, the present invention is not limited thereto. For example, feature vectors of color data and shape data may be separately formed on feature spaces in order to carry out training and identification. In this case, trainings are separately carried out on color data and shape data of colonies and classes Ccolor and Cshape of colonies are separately classified on different feature spaces. In the identifying step, the feature extracting section 51 first carries out a feature extraction computing according to a function algorithm using color data (values of R, G and B) entered to the classifier 45 as input variables to form the feature vector xj=(xr, xg, xb) (inspection point). When the classifier 45 is SVM, a high-dimensional feature vector $\psi(xj)$ is formed by mapping the point xj specified by the feature vector on the high-dimensional feature space. It is followed by determining whether or not the obtained point xj (in cases of MLP and GMM) or point $\psi(xr, xg, xb)$ (in case of SVM) belongs to the class Ccolor of colonies. When the point xj or point $\psi(xr, xg, xb)$ belongs to the class Ccolor, the point xj is identified as a colony candidate. Shape data of the colony candidate is then entered on the classifier 45. The feature extracting section 51 carries out a feature extraction computing according to a function algorithm using shape data as input variables to form a feature vector xj=(xshape) (inspection point). When the classifier 45 is SVM, a high-dimensional feature vector $\psi(xj)$ is formed by mapping the point xj specified by the feature vector on the high-dimensional feature space. It is then determined whether or not the obtained point xj (in cases of MLP and GMM) or point $\psi(xshape)$ (in case of SVM) belongs to the class Cshape of colonies. When the point xj or point $\psi(xshape)$ belongs to the class Cshape, it is identified that the point xj is a colony.

In both of the above two methods, colonies and foreign substances (fruit skin and the like) are identified due to the difference in shape in the identifying step. Because of this, the discrimination step can be omitted. In addition, colony detection accuracy is improved compared to the method using the discrimination step.

The above embodiments are not limited to the above and may be modified as follows.

An additional element of input data may be area data. The area (e.g., number of pixels) of the region specified by the same manner as shape data in the fourth embodiment can be determined. Input data containing the area data as an element is entered to the classifier 45. A feature vector x=(xr, xg, xb, xshape, xarea) or x=(xr, xg, xb, xarea) (input point or inspection point) is then obtained. The feature extracting section 51 in the classifier 45 forms the feature vector xj (inspection point) from input data containing at least area data and color data. When the classifier 45 is SVM, the mapping section 52 forms a high-dimensional feature vector point $\psi(xj)$ by mapping the inspection point xj specified by the feature vector on the high-dimensional feature space. It is determined whether or not the point xj specified by the obtained feature vector (in cases of MLP and GMM) or the point $\psi(xj)$ specified by the high-dimensional feature vector (in case of SVM) belongs to the class of colonies and colonies are identified based on the result of the determination.

In the discrimination step, at least one of shape discrimination, color discrimination and position discrimination may be employed. One or two of shape discrimination, color discrimination and position discrimination may also be employed. The discrimination step may also be omitted.

A subject for learning on the medium is not limited to the medium during a predetermined period before production of microbial colonies in the inspection subject (sample S) (training period). The subject for learning the medium may be (a) a part of medium in an image to be inspected, (b) a part of medium in an image of actual colonies of the same variation (an image of a sample that has been cultivated in advance and contains colonies or an image of a inferior sample captured in the past) or (c) a part of medium in an image of artificially prepared colonies. A subject for learning colonies may include (a) a part of colonies in an image of actual colonies of the same variation (an image of a sample that has been cultivated in advance and contains colonies or an image of an inferior sample captured in the past) or (b) a part of colonies in an image of artificially prepared colonies.

The inspection subject region is not limited to the main region A1 and may be the whole region of the medium region.

Input data are not limited to the ones for pixel unit and may be the ones for region unit containing more than one pixel.

The microorganism detecting method may be used for the purposes other than inspection. It may be used in the application in which experimental data are obtained during development of foods and beverages.

Training may be carried out on the whole region of the medium. When the medium does not contain noise N, for example, learning by the classifier 45 can be carried out on the whole region of the medium.

The notification means for issuing a notification of the detection result of colonies may be, other than display means such as a monitor, a speaker, a lamp, a printer and the like.

The transporting robot may be a 3-axis orthogonal robot. The 3-axis orthogonal robot has a traveling platform, which can travel in a horizontal direction (X direction) along a large shelf, an elevating platform, which can ascend and descend in the vertical direction (Z direction) relative to the traveling platform, and a holding member (chuck member), which can move in and out in the direction (Y direction) toward the shelf from the elevating platform. By using the 3-axis orthogonal robot, a sample can be fed to and discharged from any section of the shelf.

Microorganisms may be not only eubacteria and archaea but also eukaryotes (algae, protists, fungi, slime molds) and the like. The microorganisms may be in the size whose colonies can be seen by the naked eye or which requires microscopic observation.

The first to fourth embodiments may be used in combination. For example, in the second embodiment, the classifier may be trained on the medium points as in the first embodiment.

The invention claimed is:

1. A microorganism detecting method for detecting a microbial colony cultivated in a medium, the method comprising a training step and an identifying step, wherein
   the training step includes:
   capturing a color image of a learning subject with or without a microbial colony within a medium region, setting at least a part of the medium region as a training subject region within the captured color image;
   obtaining, as learning data, color data of either or both of medium points and microorganism points within the training subject region;
   supplying the learning data to a classifier to obtain feature vectors of the color data; and
   separating, by the classifier, a set of points specified by the feature vectors to classify at least one of a class of medium and a class of microorganisms, and
   the identifying step includes:
   supplying, to the trained classifier, color data of each inspection point within an inspection subject region corresponding to at least a part of the medium region in a color image of an inspection subject captured in order to inspect the presence or absence of a microbial colony in the medium region, thereby obtaining a feature vector of the color data;
   determining, by the classifier, to which class a point specified by the feature vector belongs among the classes classified in the training step; and
   identifying a colony based on the result of the determination.

2. The microorganism detecting method according to claim 1, wherein
   in the training step,
   the color data of the medium points within the training subject region in the captured color image of the learning subject without a microbial colony in the medium region is supplied to the classifier as the learning data to obtain feature vectors of the color data, and
   the class of medium is classified by the classifier, by setting a threshold at a position distant outward by a predetermined distance from a set of points specified by the feature vectors, and
   in the identifying step,
   color data of each inspection point within the inspection subject region in the captured color image of the inspection subject is supplied to the trained classifier to obtain a feature vector of the color data,
   it is determined, by the classifier, whether or not the inspection point specified by the feature vector belongs to the class of medium, and
   a colony is identified based on the inspection point that has been determined to not belong to the class of medium.

3. The microorganism detecting method according to claim 1, wherein
   in the training step,
   the color data of the medium points and the color data of the microorganism points within the training subject region in the captured color image of the learning subject are supplied to the classifier as the learning data to obtain feature vectors of the color data, and
   a set of medium points and a set of microorganism points specified by the feature vectors are separated by the classifier to classify the class of the medium and the class of microorganisms, and
   in the identifying step,
   color data of each inspection point within the inspection subject region in the captured color image of the inspection subject is supplied to the trained classifier to obtain a feature vector of the color data,
   it is determined, by the classifier, to which of the class of medium and the class of microorganisms the inspection point specified by the feature vector belongs, and
   a colony is identified based on the inspection point that has been determined to belong to the class of microorganisms.

4. The microorganism detecting method according to claim 1, wherein in the training step and the identifying step, the data supplied to the classifier includes, in addition to the color data, at least one of shape data and area data.

5. The microorganism detecting method according to claim 1, wherein
   in the training step, separately from the classification of the classes, noise data on noise points within the medium region are collected, and
   in the identifying step, it is discriminated whether or not the inspection point belonging to the class of microorganisms is the noise point based on the noise data, and
   a colony is identified based on the inspection point that has been discriminated not to be the noise point.

6. The microorganism detecting method according to claim 1, wherein
   in the identifying step, the medium region is divided into a peripheral region and a central region,
   the identification is carried out using the central region of the medium as the inspection subject region, and
   the colony is detected for the peripheral region based on a color edge detected by color edge detection.

7. The microorganism detecting method according to claim 2, wherein
   in the training step, the inspection subject during a predetermined period from the start of cultivation until before production of a colony is used as the learning subject in order to train the classifier for learning the medium points, thereby classifying the class of medium, and
   in the identifying step, a captured color image of the inspection subject after the predetermined period is used.

8. A microorganism detecting device for inspecting presence or absence of a microbial colony cultivated in a medium, the device comprising training means and identifying means, wherein
   training means
   captures a color image of a learning subject with or without a microbial colony within a medium region, setting at least a part of the medium region as a training subject region within the captured color image,
   obtains, as learning data, color data of either or both of medium points and microorganism points within the training subject region,
   has a classifier, and
   supplies the learning data to the classifier to obtain feature vectors of the color data,
   wherein the classifier separates a set of points specified by the feature vectors to classify at least one of a class of medium and a class of microorganisms, and
   the identifying means
   supplies, to the trained classifier, color data of each inspection point within an inspection subject region corresponding to at least a part of the medium region in a color image of an inspection subject captured in order to inspect the presence or absence of a microbial colony in the medium region, thereby obtaining a feature vector of the color data, determines, by the classifier, to which class a point specified by the feature vector belongs among the classes classified by the training means, and identifies a colony based on the result of the determination.

9. A computer configured to cause a program to execute a microorganism detection process for detecting a microbial colony cultivated in a medium, the program causing the computer to execute a training step and an identifying step, wherein the training step includes capturing a color image of a learning subject with or without a microbial colony within a medium region, setting at least a part of the medium region as a training subject region within the captured color image;

obtaining, as learning data, color data of either or both of medium points and microorganism points within the training subject region;

supplying the learning data to a classifier to obtain feature vectors of the color data; and separating, by the classifier, a set of points specified by the feature vectors to classify at least one of a class of medium and a class of microorganisms, and the identifying step includes: supplying, to the trained classifier, color data of each inspection point within an inspection subject region corresponding to at least a part of the medium region in a color image of an inspection subject captured in order to inspect the presence or absence of a microbial colony in the medium region, thereby obtaining a feature vector of the color data;

determining, by the classifier, to which class a point specified by the feature vector belongs among the classes classified in the training step; and identifying a colony based on the result of the determination.

10. The microorganism detecting method according to claim 1, wherein in the identifying step, the area of a colony candidate corresponding to a closed region containing a series of inspection points determined to belong to the class of microorganisms is determined, and when the area fulfills area conditions defined according to the species of microorganisms, the colony candidate is identified as a colony.

11. The microorganism detecting method according to claim 4, wherein in the training step and the identifying step, at least the color data and the shape data are supplied to the classifier, in the training step, color data and shape data of the colony are supplied to the classifier as learning data to obtain feature vectors of the color data and the shape data, and the class of colonies is classified by the classifier by separating a set of points specified by the feature vectors, and in the identifying step, the inspection point is a colony candidate point represented by a region distinguished by color within the inspection subject region, color data and shape data of the colony candidate point are supplied to the trained classifier to obtain feature vectors of the color data and the shape data, it is determined by the classifier whether or not a point specified by the feature vectors belongs to the class of colonies, and a colony is identified based on the result of the determination.

12. The microorganism detecting method according to claim 1, wherein the classifier includes at least one of a support vector machine based on Kernel method, a neural network, and a Gaussian mixture model.

13. The microorganism detecting method according to claim 1, wherein the classifier is a support vector machine based on Kernel method, in the training step, high-dimensional feature vectors are obtained by mapping feature vectors of color data of either or both of the medium points and the microorganism points on a high-dimensional feature space according to Kernel method by using a mapping section of the classifier, and a set of points specified by the high-dimensional feature vectors is linearly separated by the classifier to classify at least one of the class of medium and the class of microorganisms, and in the identifying step, a high-dimensional feature vector is obtained by mapping the feature vector of the color data of the inspection point on a high-dimensional feature space according to Kernel method by using the mapping section of the classifier, it is determined by the classifier to which class a point specified by the high-dimensional feature vector belongs among the classes classified in the training step, and a colony is identified based on the result of the determination.

14. The microorganism detecting device according to claim 8, comprising:

image capturing means for obtaining the color image; and notification means, which issues a notification that a colony has been detected when the identification means identifies a colony.

* * * * *